(12) United States Patent
Auger et al.

(10) Patent No.: US 9,192,604 B2
(45) Date of Patent: Nov. 24, 2015

(54) METHOD OF ADMINISTRATION AND TREATMENT

(75) Inventors: Kurt R. Auger, Collegeville, PA (US); Mohammed M. Dar, Research Triangle Park, NC (US); Ronald A. Fleming, Research Triangle Park, NC (US)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 138 days.

(21) Appl. No.: 14/128,007

(22) PCT Filed: Jun. 28, 2012

(86) PCT No.: PCT/US2012/044618
§ 371 (c)(1),
(2), (4) Date: Dec. 20, 2013

(87) PCT Pub. No.: WO2013/003575
PCT Pub. Date: Jan. 3, 2013

(65) Prior Publication Data
US 2014/0128434 A1 May 8, 2014

Related U.S. Application Data

(60) Provisional application No. 61/501,869, filed on Jun. 28, 2011.

(51) Int. Cl.
*A61K 31/4439* (2006.01)
*A61K 31/535* (2006.01)
*G01N 33/574* (2006.01)

(52) U.S. Cl.
CPC ............ *A61K 31/4439* (2013.01); *A61K 31/535* (2013.01); *G01N 33/57407* (2013.01)

(58) Field of Classification Search
CPC .................................................. A61K 31/4439

USPC .......................................................... 514/341
See application file for complete search history.

(56) References Cited

FOREIGN PATENT DOCUMENTS

WO   WO 2010/062578 A1   6/2010
WO   WO 2011/019943 A1   2/2011

OTHER PUBLICATIONS

International Search Report, which was completed on Sep. 19, 2012 in International Application No. PCT/US2012/044618.
Poulikakos, et al., "Re-expression of the tumor suppressor NF2/merlin inhibits invasiveness in mesothelioma cells and negatively regulates FAK", Oncogene, 25(44):5960-5968 (2006).

*Primary Examiner* — Raymond Henley, III
(74) *Attorney, Agent, or Firm* — Elizabeth J. Hecht; Edward R. Gimmi

(57) ABSTRACT

This invention relates to a method of treating cancer in a human in need thereof by determining the presence or absence of a detectable amount of a gene product of the Neurofibromin-2 (NF2) gene in a sample from the human, and administering to the human an effective amount of a focal adhesion kinase (FAK) inhibitor, or a pharmaceutically acceptable salt thereof, if no gene product or no isoform 1 gene product is detected. This invention also relates to a method of treating cancer in a human in need thereof, comprising determining the presence or absence of a detectable amount of a functional isoform 1 protein of the NF2 gene, or a functional fragment thereof, in a sample from the human, and administering to the human an effective amount of a focal adhesion kinase (FAK) inhibitor, or a pharmaceutically acceptable salt thereof, if no gene product or no isoform 1 gene product is detected.

16 Claims, 6 Drawing Sheets

Merlin detection in mesothelioma cell lines. A) Detection of merlin isoforms with a pan-merlin antibody. Isoform 1 is 595 amino acids and has a slower mobility while isoform 2 is 590 amino acids. B) Detection of isoform 1 of merlin (arrows indicate the presence of merlin isoform 1 protein).

Levels of FAK and pFAK in mesothelioma cell lines grown in the methylcellulose anchorage-independent conditions. A) Whole cell lysates probed for FAK in the NF2 mutant NCI-H2052 and NF2 wild-type MSTO-211H human cell lines. B) the level of pFAK (Y397) in the cell lines.

Immunohistochemistry for isoform 1 of the NF2 gene product (merlin). Standard IHC analysis of 5 mesothelioma and 1 lung cell line. Three cell lines were positive as shown in the left panel and 3 cell lines were negative, right panel.

METHOD OF ADMINISTRATION AND TREATMENT

This application is the US National Stage of International Application No. PCT/US2012/044618, filed Jun. 28, 2012, which in turn claims benefit of the earlier filing date of U.S. Provisional Application No. 61/501,869, filed Jun. 28, 2011, each of which applications are incorporated herein by reference in their entirety.

FIELD OF THE INVENTION

This invention relates to methods of treating cancers.

BACKGROUND OF THE INVENTION

Focal Adhesion Kinase (FAK herein) is a non-receptor protein tyrosine kinase that has both signaling and scaffolding functions in focal adhesions. FAK is a central regulator of cell adhesion, migration, and survival. As such, FAK inhibition provides an important avenue for treating a number of cancers. In treatment, it is important to identify patients who will respond to FAK inhibitors from those who will not, so that non-responders can be provided alternative treatment.

BRIEF DESCRIPTION OF THE FIGURES

FIG. 1A shows multiple NF2 isoforms, where FIG. 1B shows only isoform 1 of NF2.

SUMMARY OF THE INVENTION

Figure 1:
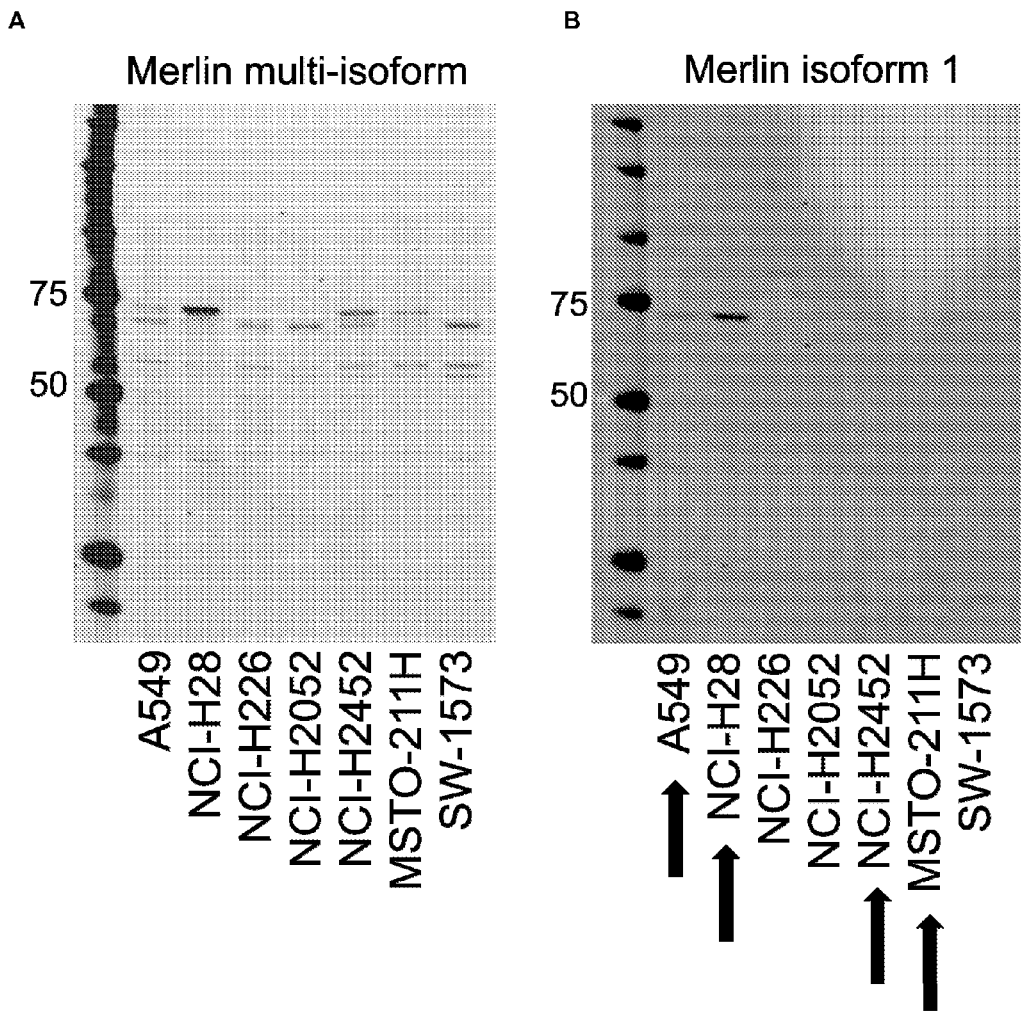
FIG. 1 shows images of a western blot detection of the gene products (protein) of NF2 in various cell lines by western blotting.

This invention relates to a method of treating cancer in a human in need thereof, comprising determining the presence or absence of a detectable amount of a gene product of the Neurofibromin-2 (NF2) gene in a sample from said human, and administering to said human an effective amount of a focal adhesion kinase (FAK) inhibitor, or a pharmaceutically acceptable salt thereof, if no gene product or no isoform 1 gene product is detected. This invention also relates to a method of treating cancer in a human in need thereof, comprising determining the presence or absence of a detectable amount of a functional isoform 1 protein of the NF2 gene, or a functional fragment thereof, in a sample from said human, and administering to said human an effective amount of a focal adhesion kinase (FAK) inhibitor, or a pharmaceutically acceptable salt thereof, if no gene product or no isoform 1 gene product is detected.

DETAILED DESCRIPTION

The extracellular matrix (ECM) provides context and framework for cellular organization in the tissues and organs of the body. The interactions between the ECM and cells of the tissue have important roles in the control of development, homeostasis, cell growth, and cell survival. Aberrant interactions between the cell and ECM or between cell-cell interactions can result in altered structure, enhanced cell migration, invasion, and growth properties ultimately leading to the development of human disease. Cancer is a prime example of human disease with deregulated cell migration and growth developing to invasive and metastatic disease.

Cellular interaction with the ECM involves cell adhesion through engagement of cellular receptors by components of the ECM. ECM binding, or more specifically fibronectin binding to the transmembrane integrin family of proteins, forms dynamic clusters of proteins at this ECM-cell interface commonly referred to as focal adhesion complexes (or focal contacts). These complexes link the ECM to the cellular cytoskeleton. The formation of a structural and signaling complex at this interface has important regulatory roles for the cell. A number of proteins with scaffolding and signaling properties have been described to localize to focal adhesions. The non-receptor protein tyrosine kinase, Focal Adhesion Kinase (FAK), also known as PKT2 or protein tyrosine kinase 2, has both signaling and scaffolding functions in focal adhesions and has been shown as a central regulator of the complex, cell adhesion, migration, and survival [1-3].

FAK was discovered independently by investigators working to understand the control of integrin-dependent cell adhesion to gain insight into anchorage-dependent cell growth, and in the case of tumor cells, anchorage-independent cell growth [4, 5]. Other investigators were pursuing substrates of the v-src oncogene to understand its mechanism(s) of transformation. The discovery of FAK as a substrate and binding partner of src in focal adhesions provided the initial insights to understanding the mechanism for anchorage-independent cell growth and protection from anoikis [6, 7]. Numerous studies have since linked FAK expression levels and/or activation state to cancer development and progression. The activation of FAK is often inferred by the level of phosphorylated or phosphor-FAK (pFAK) and more specifically, the amount of pFAK with phosphorylation on tyrosine 397, the autophosphorylation site of FAK that is also the binding site for src. Higher levels of pFAK have been associated with the transition of early stages of cancer to more advanced stages and importantly, metastatic disease [3, 8, 9].

2-[(5-chloro-2-{[3-methyl-1-(1-methylethyl)-1H-pyrazol-5-yl]amino}-4-pyridinyl)amino]-N-(methyloxy)benzamide (herein after "Compound A"), or a pharmaceutically acceptable salt thereof, is disclosed and claimed, along with pharmaceutically acceptable salts thereof, as being useful as an inhibitor of FAK activity, particularly in treatment of cancer, in International Application No. PCT/US2009/062163, having an International filing date of Oct. 27, 2009; International Publication Number WO2010/062578 and an International Publication date of Jun. 3, 2010, the entire disclosure of which is hereby incorporated by reference, and in which Compound A is the compound of example 41a.

Other compounds that are useful as inhibitors of FAK activity are described in international Application No. PCT/US/2008003235, having an international filing date of Mar. 10, 2008, International Publication Number WO2008/115369, and an International Publication date of Sep. 25, 2008, the entire disclosures of which is hereby incorporated by reference.

Compound A is being tested in human as a new cancer treatment. It is desirable to identify genotypes and phenotypes that are more likely to respond to FAK inhibitors, such as Compound A.

Neurofibromatosis type 2 (NF2) is an inherited cancer syndrome that results from the inherited germ line mutation of the NF2 (neurofibromin-2 or merlin) gene. The NF2 gene is a tumor suppressor, and aberrant or absent tumor suppressor function is seen in NF2 syndrome. The syndrome is characterized by patients who develop tumors of the nervous system including schwannomas, meningiomas, and ependymomas. Tumors develop with a somatic inactivation of the remaining allele. Mutation of the NF2 gene is also found in a large percentage of sporadic nervous system tumors highlighting the importance of this tumor suppresser in central nervous system cancers [10]. In addition, homozygous mutations of NF2 have also been identified in other tumor types including malignant mesothelioma (50%), thyroid (17%), bladder (11%), skin (5%), stomach (5%), bone (3%), kidney (2%), breast (2%), and intestine (2%) [11]. And finally, the protein product of the NF2 gene (often called merlin) has been implicated as an important regulator of glial cell growth by regulating src binding to ErbB2 and impacting the src-FAK pathway [12]. These observations suggest merlin could have a role in glioblastoma.

The protein product of the NF2 gene is most commonly referred to as merlin, but is also known as neurofibromin-2 protein. Multiple isoforms of merlin have been described and isoform 1 and isoform 2 are the most common [13]. Isoform 1 has been reported to harbor the tumor suppressor activity of NF2 and differs from isoform 2 by alternative splicing of exon 16 and exon 17 resulting in distinct carboxyl ends of the proteins. Numerous studies have identified transmembrane and intracellular proteins that interact with merlin, some through conserved domains, including the tri-lobular amino terminal Four point one, Ezrin, Radixin, Moesin (FERM) domain. These interactions are important for cytoskeletal control, cell motility, and cell invasion. Merlin also interacts with proteins proximal in the HIPPO signaling pathway, a pathway conserved in mammals yet elucidated in *Drosophila melanogaster* [14]. The HIPPO pathway is involved in cell proliferation, cell survival, and organ size. The HIPPO pathway control of these cellular activities allows merlin to exert influence on cancer cell growth and progression [13].

Malignant mesothelioma is a highly aggressive and fatal disease often associated with exposure to asbestos [15]. Mesothelioma tumors are characterized as very invasive and in approximately 40-50% of the cases, the NF2 gene is either mutated or lost by chromosomal alterations at chromosome 22q12. Forced expression of merlin in mesothelioma cells deleted of NF2 was shown to inhibit cell mobility and invasiveness. Merlin re-expression has also been shown to decrease FAK phosphorylation and disrupt binding to src and p85, the regulatory subunit of phosphoinositide 3-kinase. These studies suggest that inactivation of merlin leads to FAK activation and could be an important step in mesothelioma pathogenesis [16].

The present disclosure concerns the discovery that certain NF2 mutant cancer cells or merlin negative cancer cells are much more sensitive to FAK inhibitors than their wild type counterparts; therefore, the efficacy of an FAK inhibitor can be improved by pre-selecting patients based on their NF2 mutation status or merlin isoform 1 expression status, for example based on the presence or absence of a gene product of NF2, such as merlin isoform 1 protein.

NF2 Gene and NF2 Gene Mutations

The present disclosure relates a method of treating cancer which comprises administering an effective amount of an FAK inhibitor, or a pharmaceutically acceptable salt thereof, in a pharmaceutically acceptable composition, to a human suffering from a cancer which has one or more NF2 mutations. The present disclosure also relates to a method of treating cancer in a human in need thereof, comprising administering an effective amount of a FAK inhibitor or pharmaceutically acceptable salt thereof to the human in need of treatment, wherein the human was determined to have a cancer with at least one Neurofibromin 2 (NF2) mutation, or any mutation that results in the absence of a detectable amount of the gene products of the NF2 gene, e.g. merlin isoform 1 protein, or any mutation that results in the absence of a detectable amount of functional gene products of the NF2 gene, e.g. functional merlin isoform 1 protein or fragment thereof. Administration of FAK inhibitors to humans with cancers with at least one Neurofibromin 2 (NF2) mutation, or any mutation that results in the absence of a detectable amount of the gene products of the NF2 gene, e.g. merlin isoform 1 protein, or any mutation that results in the absence of a detectable amount of functional gene products of the NF2 gene, e.g. functional merlin isoform 1 protein or fragment thereof, results in the enhancement of one or more symptoms, as compared to humans without such mutations.

Expression of the wild-type NF2 gene (NM_000268 and Gene ID: 4771) results in expression of multiple gene products, i.e. multiple isoforms. For example, expression of the wild-type NF2 gene results in expression of at least isoform 1 and isoform 2 of the NF2 gene. Expression of an NF2 gene that is not wild-type, because it has one or more mutations, can result in lack of expression of the gene products of one or more isoforms of the NF2 gene. In certain embodiments, a mutation in the NF2 gene, i.e. an NF2 mutation, results in one or more gene products, or fragments thereof, not being expressed, either into mRNA or into protein. In certain embodiments, the sample, which is obtained from a human in need of cancer treatment, contains cells that have an NF2 mutation, wherein the mutation results in detectable mRNA transcripts that are not translated into protein, such a mutation that results in a premature stop codon. In other embodiments, an NF2 mutation results in lack of expression of mRNA and translated protein, e.g. because the NF2 mutation resulted from chromosomal loss or other deletion of the NF2 gene. In other embodiments, the NF2 mutation, e.g., because of chromosomal loss, deletion of the NF2 gene, or a mutation resulting in a premature stop codon, results in lack of expression of, or the absence of detectable amounts of, isoform 1 of NF2.

In further embodiments, the NF2 mutation results in lack of expression of a protein expressed by the NF2 gene, where the protein is a tumor suppressor isoform. In another embodiment, the tumor suppressor isoform that is not expressed is isoform 1 of NF2. In another embodiment, the mutation in the NF2 gene results in the lack of expression of the isoform 1 gene product of NF2. In a further embodiment, the isoform 1 protein gene product of the mutant NF2 gene is not expressed. In another embodiment, the isoform 1 protein gene product of the mutant NF2 gene is not present in a detectable amount. In a further embodiment, a functional fragment of the isoform 1 protein gene product of NF2, i.e. a fragment that retains tumor suppressor activity as measured in vivo or in vitro, is not present in a detectable amount.

In other embodiments, the gene products of the NF2 gene may be expressed, i.e. present in a detectable amount, but nevertheless the gene product may not be functional. The loss of function of a gene product can occur in any number of ways, and includes mutation Accordingly, this invention also relates to a method of treating cancer in a human in need thereof, comprising determining the presence or absence of a detectable amount of a functional isoform 1 protein of the NF2 gene, or a functional fragment thereof, in a sample from said human, and administering to said human an effective amount of a focal adhesion kinase (FAK) inhibitor, or a pharmaceutically acceptable salt thereof, if no gene product or no isoform 1 gene product is detected.

In some embodiments where NF2 mutations are detected in a cancer obtained from a human, a FAK inhibitor is administered. In the methods herein in which there is a lack of expression of a tumor suppressor isoform, such as lack of expression of isoform 1 of NF2, the method comprises administering a FAK inhibitor, or a pharmaceutically acceptable salt thereof, to the human with cancer. One embodiment is a method of treating cancer in a human in need thereof, comprising detecting the expression of one or more isoforms of the NF2 gene in said cancer and administering an effective amount of a FAK inhibitor, or a pharmaceutically acceptable salt thereof, if no tumor suppressor isoform is detectably expressed. Another embodiment herein is a method of treating cancer in a human in need thereof, comprising obtaining a sample of one or more cells of said cancer, detecting the expression of isoform 1 of NF2 in said sample, and, if said isoform 1 of NF2 is not detected, administering an effective amount of a FAK inhibitor or a pharmaceutically acceptable salt thereof. In a further embodiment wherein isoform 1 of NF2 is not detected, said detection is of the isoform 1 protein gene product of the NF2 gene. Yet another embodiment herein is a method of treating cancer in a human in need thereof, comprising obtaining a sample of one or more cells of said cancer, detecting the presence or absence of isoform 1 and one or more additional isoforms of NF2 in said sample, and if isoform 1 is not detected, administering an effective amount of a FAK inhibitor or a pharmaceutically acceptable salt thereof.

In other embodiments, the isoform 1 of wild-type NF2 is expressed in the tumor, or sample thereof, from a human in need of cancer treatment. In a further embodiment, the wild-type isoform 1 gene product of the NF2 gene is present in a detectable amount. In yet a further embodiment, a fragment of the isoform 1 of the wild-type NF2 is present in a detectable amount. In a further embodiment, the fragment of the isoform 1 gene product of the NF2 gene is a functional fragment, where the fragment of the isoform 1 gene product of NF2 retains tumor suppressor activity in vitro or in vivo, or both. In certain embodiments where the isoform 1 gene product of NF2 is protein, or a functional fragment thereof, and the isoform 1 protein is present in detectable amounts in a human sample, the human is treated with 2-[(5-chloro-2-{[3-methyl-1-(1-methylethyl)-1H-pyrazol-5-yl]amino}-4-pyridinyl)amino]-N-(methyloxy)benzamide, or a pharmaceutically acceptable salt thereof, and the method further comprises enhanced monitoring of the cancer. In certain embodiments where the isoform 1 gene product of NF2 is protein, or a functional fragment thereof, and the isoform 1 protein is present in detectable amounts in a human sample, the human is treated with 2-[(5-chloro-2-{[3-methyl-1-(1-methylethyl)-1H-pyrazol-5-yl]amino}-4-pyridinyl)amino]-N-(methyloxy)benzamide in combination with other anti-cancer agents, and the method further comprises enhanced monitoring of the cancer.

In an alternative embodiment, the presence or absence of a detectable amount of an isoform 1 gene product of NF2 in a sample obtained from a human in need of cancer treatment is used as a biomarker, wherein the absence of a detectable amount of isoform 1 of NF2 in said sample indicates the human is suitable for treatment with a FAK inhibitor. In a further embodiment, the presence or absence of a detectable amount of an isoform 1 gene product of NF2 in a sample obtained from a human in need of cancer treatment is used as a biomarker, wherein the gene product is protein, and wherein absence of a detectable amount of neurofibromin 2 isoform 1 protein in said sample indicates the human is suitable for treatment with a FAK inhibitor. In a further embodiment, the presence or absence of a detectable amount of the isoform 1 gene product of NF2, such as neurofibromin 2 isoform 1 protein, in a sample obtained from a human in need of cancer treatment is used as a biomarker, wherein the absence of a detectable amount of neurofibromin 2 isoform 1 protein in said sample indicates the human is suitable for treatment with a FAK inhibitor, wherein the FAK inhibitor is 2-[(5-chloro-2-{[3-methyl-1-(1-methylethyl)-1H-pyrazol-5-yl]amino}-4-pyridinyl)amino]-N-(methyloxy)benzamide, and wherein the cancer treatment is for mesothelioma.

Merlin Isoform 1

The protein gene product of the NF2 gene is often called merlin (UniProt No. P35240), and is also known as neurofibromin-2. Accordingly, one of skill in the art would recognize that merlin isoform 1 protein is the same as neurofibromin-2 isoform 1 protein and NF2 isoform 1 protein. The isoform 1 protein gene product of NF2, or merlin isoform 1 protein, is known in the art to have tumor suppressor function. Merlin isoform 1 protein can be referred to in shorthand as merlin; whether merlin refers to merlin isoform 1 or multiple isoforms should be clear from context. Herein, cells (e.g. tumor cells) in which there is an absence of a detectable amount of merlin isoform 1 protein are referred to as "merlin negative." Herein, a cancer is a "merlin negative cancer" if a there is an absence of a detectable amount of merlin isoform 1 protein in the cancer or tumor, or in at least a proportion of the cancer cells, e.g. a portion of the cancer cells that were obtained as a sample from a human in need of cancer treatment. Herein, cells (e.g. tumor cells) in which there is an absence of a detectable amount of functional merlin isoform 1 protein are likewise referred to as merlin negative. Herein, a cancer is also a merlin negative cancer if a there is an absence of a detectable amount of functional merlin isoform 1 protein in the cancer or tumor, or in at least a proportion of the cancer cells, e.g. a portion of the cancer cells that were obtained as a sample from a human in need of cancer treatment.

The absence of a detectable amount of a merlin isoform 1 protein may result from a mutation in the NF2 gene, as described above. The absence of a detectable amount of a merlin isoform 1 protein may result from abnormal transcription or translation, or from various post transcriptional or post-translational processes, both normal and abnormal. The absence of a detectable amount of a merlin isoform 1 protein may result from a mutation in the promoter or other regulatory sequences necessary for the transcription of merlin isoform 1 mRNA. In addition, the absence of a detectable amount of a merlin isoform 1 protein may be due to various epigenetic phenomena; for example, merlin isoform 1 protein may be suppressed by epigenetic mechanisms. The absence of a detectable amount of merlin isoform 1 protein may be the result of genetic modification(s), including but not limited to, alterations, mutations, deletions, insertions, and the like, in one or more other genes that are not the NF2 gene, but that are required for merlin expression (e.g. merlin isoform 1 mRNA or protein expression) including but not limited to factors required for transcription, splicing, translation, or protein stability.

In some embodiments herein, a merlin isoform 1 protein may be present in a detectable amount, but the merlin isoform 1 protein is not functional. The absence of a detectable amount of a functional merlin isoform 1 protein may occur for any number of reasons, such as a mutation, abnormal transcription or translation, or abnormal post transcriptional or post translational processing. Cancer cells having a loss of function of merlin isoform 1 protein will likely exhibit the same phenotype as cancer cells having an absence of detectable amounts of a merlin isoform 1 protein; this phenotype will allow for improved treatment with a FAK inhibitor, or a pharmaceutically acceptable salt thereof, disclosed herein in a human having such cancer cells, e.g. as compared to a human with a cancer that has a functional merlin isoform 1 protein. This phenotype may also include elevated levels of pFAK expression.

Establishing a loss of function of a merlin isoform 1 protein is within the skill of one in the art, and includes, but is not limited to measuring downstream signaling by merlin protein. One such pathway of downstream signaling is the canonical pathway involving MST1/2 and LATS1/2 kinases that regulate the transcription factors YAP/TAZ. Measuring the downstream signaling optionally includes determining the phosphorylation status and/or the phosophorylation levels of the targets of the kinases (e.g. MST1/2 and/or LAT1/2). Measuring the downstream signaling optionally includes measuring the expression levels of the target genes of the YAP/TAZ transcription complex. Measuring the downstream signaling of a kinase pathway in which merlin is involved is within the skill of one in the art.

One embodiment herein is a method of treating cancer in a human in need thereof comprising determining the presence or absence of a detectable amount of merlin isoform 1 protein or a functional fragment thereof from a tumor sample from said human, and administering to said human an effective amount of 2-[(5-chloro-2-{[3-methyl-1-(1-methylethyl)-1H-pyrazol-5-yl]amino}-4-pyridinyl)amino]-N-(methyloxy)benzamide, or a pharmaceutically acceptable salt thereof, if no merlin isoform 1 protein or functional fragment thereof is detected.

Another embodiment is a method of treating merlin negative cancer in a human in need thereof comprising administering a therapeutically effective amount of a FAK inhibitor to said human. In a further embodiment of the method of treating merlin negative cancer in a human, the FAK inhibitor is 2-[(5-chloro-2-{[3-methyl-1-(1-methylethyl)-1H-pyrazol-5-yl]amino}-4-pyridinyl)amino]-N-(methyloxy)benzamide, or a pharmaceutically acceptable salt thereof.

In an alternative embodiment, the presence or absence of a detectable amount of merlin isoform 1 protein or functional fragment thereof in a sample obtained from a human in need of cancer treatment is used as a biomarker, wherein the absence of a detectable amount of merlin isoform 1 protein or functional fragment thereof in said sample indicates the human is suitable for treatment with a FAK inhibitor. In a further embodiment, the presence or absence of a detectable amount of merlin isoform 1 protein or functional fragment thereof in a sample obtained from a human in need of cancer treatment is used as a biomarker, wherein the absence of a detectable amount of merlin isoform 1 protein or functional fragment thereof in said sample indicates the human is suitable for treatment with a FAK inhibitor, wherein the FAK inhibitor is 2-[(5-chloro-2-{[3-methyl-1-(1-methylethyl)-1H-pyrazol-5-yl]amino}-4-pyridinyl)amino]-N-(methyloxy)benzamide, and wherein the cancer treatment is for mesothelioma.

pFAK

Phosphorylated FAK, or pFAK, can be over-expressed in cells, e.g. tumor cells, that have one or more NF2 mutations. For example, pFAK is overexpressed in some tumor cells that have a mutation in the NF2 gene, where the mutation in the NF2 gene results in lack of expression of the isoform 1 protein gene product of the NF2 gene. Accordingly, in some embodiments, pFAK is present in higher amounts in tumor cells in which there is an absence of a detectable amount of neurofibromin 2 isoform 1 protein or merlin isoform 1 protein. (Neurofibromin 2 isoform 1 protein refers to the same amino acid sequence as that of merlin isoform 1 protein, and each can also be referred to, among other names, as NF2 isoform 1 protein, as is known in the art and is described herein).

In one embodiment of the methods of treating cancer herein, the method comprises determining the levels of pFAK in a sample from a human in need thereof, and administering to said human an effective amount of a FAK inhibitor, or a pharmaceutically acceptable salt thereof, if elevated levels of pFAK are determined, as compared to a control sample. In a further embodiment, the control sample is prepared from normal patient tissue. In an alternative embodiment, the control sample is prepared from cells comprising a wild type NF2 gene. In yet another embodiment, multiple control samples are employed.

In another embodiment of the methods of treating cancer herein, the absence or presence of a detectable amount of isoform 1 of NF2 is determined and the levels of pFAK are determined. In a further embodiment, if elevated pFAK and no detectable amount of the isoform 1 of NF2 is observed, then a FAK inhibitor, or a pharmaceutically acceptable salt thereof is administered. In further embodiments of the methods of treating cancer comprising determining pFAK levels, the cancer is mesothelioma and the FAK inhibitor, if administered, is a FAK inhibitor of Formula I, suitably Compound A.

The Presence or Absence of a Detectable Amount of a Gene Product

Detecting the presence or absence of a gene product (e.g. isoform 1) of NF2 means establishing that a gene product (e.g., an NF2 isoform 1 protein, a neurofibromin-2 isoform 1 protein, or a merlin isoform 1 protein) is likely expressed in a sample, and for example, can be detected at levels above background noise in any particular assay used for detection. Those of skill in the art are familiar with discriminating a positive signal indicating that a gene product is expressed or present from a low or background signal. Positive and negative controls can be implemented to establish background or noise from a positive signal. For example, a "cutoff" can be established by determining the level of background noise, such as staining or other measured signal, in a negative control that does not express the gene product of interest. Thus, presence of a gene product can mean that the gene product is detected above background levels in a tissue, e.g. in one or more cells or a proportion of cells within a tissue. Conversely, the absence of a gene product means that the gene product is not measurable above background levels in a tissue, e.g. in one or more cells or a proportion of cells within a tissue.

The absence or presence of a detectable amount of a gene product, wherein the gene product is a protein, may be accomplished by any number of methods well known in the art. These methods include, but are not limited to, one or more of the following: mass spectrometry, 2D, electrophoresis, HPLC, protein sequencing, and various immunological detection methods. The immunological detection methods include, but are not limited to immunoaffinity assays, immunoprecipitation assays, immunocytochemistry assays, ELISAs, solid phase sandwich assays, immunoblotting, high throughput immunoblotting, immunohistochemistry, or a combination of these techniques.

Immunohistochemistry

Suitably, in one embodiment herein the presence or absence of a detectable amount of an isoform 1 gene product of the NF2 gene is determined by detecting protein. In a further embodiment where protein is detected, the protein is neurofibromin-2 isoform 1. In further embodiments of treating cancer, wherein protein is detected, the absence or presence of a detectable amount of neurofibromin-2 isoform 1 protein is determined by immunohistochemistry (IHC).

IHC is a process of detecting a protein in a tissue sample, such as a tumor biopsy, using one or more antibodies specific to the protein. (In this sense, the protein that an antibody specifically detects is often referred to as an antigen.) The binding of the antibody to the protein is resolved through staining and microscopy. IHC is well known in the art.

Typically, a tissue sample is obtained, which must be rapidly preserved to prevent the breakdown of cellular protein and tissue architecture. Often, the tissue is perfused, or rinsed of blood, prior to preservation. Preparation of tissue samples for IHC is also well known in the art and include, but are not limited to, paraffin-embedding, flash-freezing, formalin fixation, and formaldehyde fixation.

Prepared tissues, such as paraffin-embedded tissues, are typically sectioned into slices as thin as 4-5 μm with a microtome. These sections are then mounted onto glass slides that are coated with an adhesive. This adhesive is commonly added by surface-treating glass slides with 3-aminopropyltriethoxysilane (APTS) or poly-L-lysine. Slides may alternatively be coated with other suitable adhesives, including gelatin, egg albumin or commercially available glue. After mounting, the sections are dried. Paraffin embedded slides may be dried in an oven or microwave in preparation for deparaffinization.

Frozen sections may be prepared using a pre-cooled cryostat and mounted to adhesive glass slides. These sections are often dried overnight at room temperature and fixed by immersion in pre-cooled (−20° C.) acetone, although the drying step may be omitted as determined by one of skill in the art, based on the tissue and protein to be detected.

Before staining and detection of the presence or absence of a protein in a sample, the tissue sample is "unmasked," to allow access of the antibody to the protein. This process is often called antigen retrieval, and can be accomplished by any number of means known in the art, such as heat or enzymatic means, including using trypsin, pepsin, or other proteases.

Binding of the antibody to the protein in the sample is accomplished by incubation with the antibody in any number of solutions or buffers well known in the art. Buffers may contain blocking agents, which block nonspecific binding of the antibody to the tissue; blocking may be accomplished before or during incubation of the tissue sample slide with the antibody. The amount of antibody used in the method can affect the level of signal resolved later by microscopy, and one of skill in the art would know to determine and optimize the amount of antibody to use in any particular IHC assay, e.g. by testing dilutions of the antibody.

In general, antibodies employed in IHC may be monoclonal or polyclonal. In the case of detection of neurofibromin-2 isoform 1, the antibody must be able to detect the presence or absence of the isoform 1 protein in tissue in which other isoforms may be present. So, a neurofibromin-2 isoform 1 specific antibody must be employed. The specific antibody is often a monoclonal antibody; however one of skill in the art could identify a polyclonal antibody preparation suitable for detecting the presence or absence of isoform 1 of NF2 in a sample. Suitably, in an embodiment herein, detection of the presence or absence of the isoform 1 protein gene product of the NF2 gene comprises contacting a sample with a monoclonal antibody raised against neurofibromin-2 isoform 1, where such an antibody is able to detectably bind to neurofibromin-2 isoform 1, and does not detectably bind to other neurofibromin-2 isoforms. In a further embodiment, the anti-neurofibromin-2 isoform 1 monoclonal antibody does not detectably bind to isoform 2 protein gene products NF2. In another embodiment, the antibody is a polyclonal antibody preparation, wherein the polyclonal antibody is able to bind neurofibromin-2 isoform 1 protein, but not neurofibromin-2 isoform 2 protein. In further embodiments where the monoclonal antibody or the polyclonal antibody detectably binds neurofibromin-2 isoform 1 but does not detectably bind neurofibromin-2 isoform 2, the monoclonal antibody or the polyclonal antibody also do not detectably bind other isoforms besides isoform 1.

Detection of antibody binding to the protein can be accomplished in a number of ways well known in the art such as immunoflourescent detection of an antibody tagged with a fluorofore or immunoperoxidase staining of an antibody conjugated to an immunoperoxidase enzyme. Other methods of detection well known in the art include chromogenic detection, radioactivity, chemiluminescence, and other biological and enzymatic tags or labels. Indirect detection can also be employed, and can provide advantages, such as a biotin/avidin based system and other secondary detection systems that are within the knowledge and skill in the art.

One of skill in the art may also employ counterstaining to visualize cells or cell compartments, such as the nucleus.

Genetic Detection

NF2 gene mutations may also be determined at the genetic level, either alone or in combination with determining the presence or absence of a gene product, such as protein. Such genetic testing can be accomplished by any number of means well known in the art, including, but not limited to, sequencing, RT-PCR, and in situ hybridization, such as fluorescence-based in situ hybridization (FISH).

In one embodiment according to the present disclosure, a method of treating cancer in a human in need thereof comprises detecting a mutation in the NF2 gene in a sample from said human, determining whether said mutation in the NF2 gene results in the lack of expression of isoform 1 of NF2, and administering a therapeutically effective amount of a FAK inhibitor, such as compound A herein, or a pharmaceutically acceptable salt thereof, to said human if the mutation results in lack of expression of isoform 1 of NF2. In a further embodiment, determining whether said mutation in the NF2 gene results in a lack of expression of isoform 1 of NF2 comprises performing a method selected from the following: sequencing, RT-PCR, and FISH. In another embodiment, determining whether said mutation in the NF2 gene results in a lack of expression of isoform 1 of NF2 comprises performing a method selected from the following: sequencing, RT-PCR, and FISH. Sequencing, RT-PCR, and FISH allow one of skill in the art to establish chromosomal loss or other deletion in the NF2 gene that would result in lack of expression of NF2 gene product, in particular isoform 1 protein. Sequencing and RT-PCR allow one of skill in the art to establish a point mutation, insertion, or deletion that would result in a premature stop codon and result in lack of expression of NF2 gene product, in particular isoform 1 protein.

In other embodiments according to the present invention, the determination of whether a patient has a particular mutation that would respond to a FAK inhibitor at a given gene includes:
a. performing a genotyping technique on a biological sample from the subject tumor to determine whether said patient has a tumor with at least one isoform of NF2 mutant;
b. correlating the detection of said mutations with increased likelihood of experiencing one or more of an increased response rate, longer progression free survival, or longer overall survival when administered a FAK inhibitor, optionally a FAK inhibitor of Formula I, optionally Compound A, as compared to the likelihood if said mutations were not detected.

FAK Inhibitors

In any of the methods herein for treating cancers, e.g. merlin-negative cancer or cancers in which the neurofibromin-2 isoform 1 protein is not detectable, the FAK inhibitor may be a compound of formula (I):

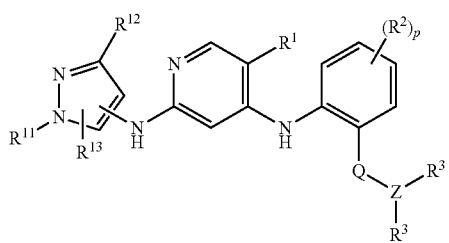

(I)

or a salt thereof, wherein:
$R^1$ is halo, $CF_3$, $C_1$-$C_6$-alkyl, isopropenyl, ($C_2$-$C_6$-alkylene) $C_3$-$C_6$-cycloalkyl, $C_1$-$C_6$-alkoxy, or cyano;
in $R^2$ when p is other than 0, each $R^2$ is independently F, Cl, $CF_3$, methyl, methoxy, $CH_2CF_3$, —$(X)_q$—$C_1$-$C_4$-alkylene-$R^4$, —$(X$—$C_1$-$C_4$-alkylene)$_q$-$NR^5$—$C(O)$—$R^6$, —$(X$—$C_1$-$C_4$-alkylene)$_q$-$(NR^5)_q$—$SO_x$—$R^7$, —$(X$—$C_1$-$C_4$-alkylene)$_q$-$Y$—$N(R^8)_2$; a 5- to 6-membered heterocycloalkyl-$(R^9)_q$ group, or a 5- to 6-membered heteroaryl-$(R^{10})_r$ group;
$R^3$ is independently H, $C_3$-$C_6$-cycloalkyl, $C_1$-$C_6$-alkyl, $C_1$-$C_6$alkoxy, $C_1$-$C_6$-alkylene-$R^4$, O—$C_1$-$C_6$-alkylene-$R^4$, or, the $R^3$ groups, together with Z, form a 5- to 6-membered cyclic ring optionally substituted with methyl, $C_1$-$C_4$-alkylene-$R^4$, or $C_3$-$C_6$-cycloalkyl;
$R^4$ is H, -$(Q)_q$-$N(R^8)_2$, OH, SH, $C_1$-$C_6$-alkoxy, $C_1$-$C_6$-thioalkyl, or a 5- to 6-membered heterocycloalkyl-$(R^9)_q$ group;
$R^5$ is H or $C_1$-$C_6$-alkyl;
$R^6$ is H, $C_1$-$C_6$-alkyl, $C_1$-$C_6$-alkoxy, $N(R^8)_2$, or a 5- to 6-membered heteroaryl-$(R^{10})_r$ group;
$R^7$ is $C_1$-$C_6$-alkyl, phenyl-$(R^9)_q$, or 5- to 6-membered heteroaryl-$(R^{10})_r$
$R^8$ is independently H, $C_1$-$C_6$-alkyl, —O—$C_1$-$C_6$-alkyl or, together with the nitrogen atom to which they are attached, form a 5- or 6-membered heterocycloalkyl group;
$R^9$ is H, $C_1$-$C_6$-alkyl, $C_1$-$C_6$-alkoxy, -$(Q)_q$-$N(R^8)_2$, -Q-$C_1$-$C_6$-alkyl, —$C_1$-$C_6$alkyl$R^4$, or 5- to 6-membered heterocyloalkyl;
$R^{10}$ is H, $C_1$-$C_6$-alkyl, $C_1$-$C_6$-alkoxy, or -Q-$C_2$-$C_6$-alkyl;
$R^{11}$ is $C_1$-$C_6$-alkyl, $CF_3$, —$CH_2CF_3$, -$(Q)_q$-$C_1$-$C_4$-alkylene-$R^4$, -Q-$N(R^8)_2$, phenyl-$(R^5)_S$, a 5- to 6-membered heterocycloalkyl-$(R^9)_q$ group, or a 5- to 6-membered heteroaryl-$(R^{10})_r$ group;

$R^{12}$ is H, $C_1$-$C_6$-alkyl, F, Cl, $CF_3$, OH, CN, nitro, COOH, —COO—$C_1$-$C_6$-alkyl, —Y—$N(R^8)_2$, $C_3$-$C_6$-cycloalkyl-$R^{14}$, —$(X)_q$—$C_1$-$C_6$-alkylene-$R^4$, —$(X$—$C_1$-$C_6$-alkylene)$_q$-$NR^5$—$C(O)$—$R^6$, —$(X$—$C_1$-$C_6$-alkylene)$_q$-$(NR^5)_q$—$SO_x$—$R^7$, —$(X$—$C_1$-$C_6$-alkylene)$_q$-$Y$—$N(R^8)_2$, heterocycloalkyl-$(R^9)_q$, heteroaryl-$(R^{10})_r$, or phenyl-$(R^{15})_S$;
$R^{13}$ is H, F, Cl, $C_1$-$C_6$-alkyl, or $C_3$-$C_6$-cycloalkyl; or $R^{12}$ and $R^{13}$, together with the carbon atoms to which they are attached, form a fused 5- or 6-membered carbocycloalkyl or heterocycloralkyl group;
$R^{14}$ is independently H, $C_1$-$C_6$-alkyl. —$NR^5$—$SO_2$—$R^7$, —Y—$N(R^8)_2$, or —$(X)_q$—$C_1$-$C_6$-alkylene-$R^4$;
$R^{15}$ is independently F, Cl, $CF_3$, $C_1$-$C_3$-alkyl, or $C_1$-$C_3$-alkoxy;
p is 0, 1, 2, or 3;
q is 0 or 1;
r is 0, 1, or 2;
s is 0, 1, 2, or 3;
x is 1 or 2;
Q is —C(O)—, —S(O)—, or —$SO_2$—;
X is $NR^5$, O, S, —S(O)—, or —$SO_2$—;
Y is a bond, $SO_2$, or C(O); and
Z is N or $CR^5$.

The present invention also relates to a methods of treating certain cancers, e.g. merlin-negative cancer or cancers in which the neurofibromin-2 isoform 1 protein is not detectable, wherein the FAK inhibitor is a compound of formula (I), and wherein Q is C(O) and Z is N.

The present invention also relates to a method of treating certain cancers, e.g. merlin-negative cancer or cancers in which the neurofibromin-2 isoform 1 protein is not detectable, wherein the FAK inhibitor is a compound of formula (I), and wherein $R^1$ is Cl, $CF_3$, or CN.

The present invention also relates to a method of treating certain cancers, e.g. merlin-negative cancer or cancers in which the neurofibromin-2 isoform 1 protein is not detectable, wherein the FAK inhibitor is a compound of formula (I), and wherein $R^2$ is F.

The present invention also relates to a method of treating certain cancers, e.g. merlin-negative cancer or cancers in which the neurofibromin-2 isoform 1 protein is not detectable, wherein the FAK inhibitor is a compound of formula (I), and wherein one $R^3$ is methyl and the other $R^3$ is H.

The present invention also relates to a method of treating certain cancers, e.g. merlin-negative cancer or cancers in which the neurofibromin-2 isoform 1 protein is not detectable, wherein the FAK inhibitor is a compound of formula (I), and wherein one $R^3$ is methoxy and the other $R^3$ is H.

The present invention also relates to a method of treating certain cancers, e.g. merlin-negative cancer or cancers in which the neurofibromin-2 isoform 1 protein is not detectable, wherein the FAK inhibitor is a compound of formula (I), and wherein $R^{11}$ is $C_1$-$C_6$-alkyl.

The present invention also relates to a method of treating certain cancers, e.g. merlin-negative cancer or cancers in which the neurofibromin-2 isoform 1 protein is not detectable, wherein the FAK inhibitor is a compound of formula (I), and wherein $R^{12}$ is $C_1$-$C_6$-alkyl, hydroxymethyl, or cyclopropyl.

The present invention also relates to a method of treating certain cancers, e.g. merlin-negative cancer or cancers in which the neurofibromin-2 isoform 1 protein is not detectable, wherein the FAK inhibitor is a compound of formula (I), and wherein $R^{13}$ is H.

The present invention also relates to a method of treating certain cancers, e.g. merlin-negative cancer or cancers in which the neurofibromin-2 isoform 1 protein is not detectable, wherein the FAK inhibitor is a compound of formula (I), and wherein p is 0 or 1.

The present invention also relates to a method of treating certain cancers, e.g. merlin-negative cancer or cancers in which the neurofibromin-2 isoform 1 protein is not detectable, wherein the FAK inhibitor is 2-[(5-chloro-2-{[3-methyl-1-(1-methylethyl)-1H-pyrazol-5-yl]amino}-4-pyridinyl)amino]-N-(methyloxy)benzamide, or a pharmaceutically acceptable salt thereof.

The present invention also relates to a method of treating certain cancers, e.g. merlin-negative cancer or cancers in which the neurofibromin-2 isoform 1 protein is not detectable, wherein the FAK inhibitor is 2-[(5-chloro-2-{[3-methyl-1-(1-methylethyl)-1H-pyrazol-5-yl]amino}-4-pyridinyl)amino]-N-(methyloxy)benzamide, hydrochloride salt.

The present invention also relates to a method of treating certain cancers, e.g. merlin-negative cancer or cancers in which the neurofibromin-2 isoform 1 protein is not detectable, wherein the FAK inhibitor is 2-[(5-chloro-2-{[3-methyl-1-(1-methylethyl)-1H-pyrazol-5-yl]amino}-4-pyridinyl)amino]-N-(methyloxy)benzamide, or a pharmaceutically acceptable salt thereof, in a pharmaceutically acceptable composition.

The present invention also relates to a method of treating certain cancers, e.g. merlin-negative cancer or cancers in which the neurofibromin-2 isoform 1 protein is not detectable, which comprises administering any one of the exemplified compounds described in WO2008/115369, wherein said cancer has at least one NF2 mutation.

One embodiment of the invention is a compound of Formula I, for the treatment of cancer in a human, wherein said cancer has no detectable amounts of a gene product of the NF2 gene. Another embodiment of the invention is a compound of Formula I, for the treatment of cancer in a human, wherein said cancer has no detectable amounts of isoform 1 of the NF2 gene. Another embodiment of the invention is a compound of Formula I, for the treatment of cancer in a human, wherein said cancer has no detectable amounts of merlin protein. In yet another embodiment of the invention is a compound of Formula I, for the treatment of cancer in a human, wherein said cancer has no detectable amounts of merlin isoform 1 protein. In further embodiments of the invention in this paragraph, the cancer is mesothelioma and the compound of Formula I is Compound A, as described herein.

The present invention relates to use of a FAK inhibitor in the manufacture of a medicament for the treatment of cancer in a human identified as suitable for said treatment, wherein said human is identified as suitable for said treatment by the absence of detectable amounts of an isoform 1 gene product of NF2 (such as neurofibromin-2 isoform 1 protein or merlin isoform 1 protein) in said cancer. Further embodiments of the invention relate to the preceding use, wherein the FAK inhibitor is compound A and the cancer is mesothelioma.

The present invention also relates to methods of identifying cancers that will respond to the FAK inhibitors described herein. In one embodiment, a method of identifying a cancer that will respond to a FAK inhibitor of Formula I comprises detecting the presence or absence of an isoform 1 gene product of the NF2 gene in a sample of said cancer, whereby a cancer that will respond to a FAK inhibitor of Formula I is identified when no isoform 1 gene product of the NF2 gene in said sample is detected. In another embodiment, a method of identifying a cancer that will respond to a FAK inhibitor of Formula I comprises:

a) Obtaining a sample of said cancer from a human in need of treatment;
b) Detecting the presence or absence of an isoform 1 gene product of the NF2 gene in said sample; and
c) Determining that said cancer can be treated with an effective amount of a FAK inhibitor of Formula I when no isoform 1 gene product of the NF2 gene is detected in said sample.

Samples

In the methods described herein, the absence or presence of a detectable amount of an isoform 1 gene product of NF2 is determined using a sample from a human in need of treatment for cancer. In other methods described herein, the absence or presence of a detectable amount of a functional merlin isoform 1 protein is determined using a sample from a human in need of treatment for cancer. The sample, as described above and below in more detail, comprises one or more suspected tumor cells, e.g. is called a tumor sample. In certain embodiments, the sample is a biopsy of suspected tumor cells. In certain embodiments, the samples may be tissue biopsies. In other embodiments, the sample is a biopsy of cells that are known to be cancerous, e.g. a tumor, based on other means of testing for cancer or confirming the status of a growth as a tumor or cancer. Other samples that may be obtained from a human in need of cancer treatment include but are not limited to a group of proteins, nucleotides, cellular blebs or components, serum, cells, blood, blood components such as circulating tumor DNA, urine and saliva.

Handling, preserving, and storage of the sample, e.g. for determining the presence or absence of a detectable amount of an isoform 1 gene product of the NF2 gene, or for determining the presence or absence of a detectable amount of a functional merlin isoform 1 protein, will depend on the particular assay employed. For example, processing for IHC, described generally herein requires certain preparation and storage conditions, which are known in the art.

Cancers

Humans having cancers in which there is an absence of a detectable amount of isoform 1 gene product of the NF2 gene, e.g. merlin isoform 1 protein, or cancers in which there is an absence of a detectable amount of functional merlin isoform 1 protein exhibit an improved response to treatment with the FAK inhibitors herein. In certain embodiments, the cancer is selected from the group consisting of schwannoma, meningioma, ependymoma. mesothelioma, glioblastoma, melanoma thyroid cancer, bladder cancer, skin cancer, stomach cancer, bone cancer, kidney cancer, breast cancer, and intestinal cancer. In other embodiments, the skin cancer is melanoma. In suitable embodiments, the cancer is mesothelioma.

Kits

In another embodiment the invention provides a kit for the treatment of cancer, such as mesothelioma, comprising a kit for detecting the presence or absence of an isoform 1 gene product of the NF2 gene in a sample, comprising: (a) a means for detecting an isoform 1 gene product of the NF2 gene, such as merlin isoform 1 protein or neurofibromin-2 isoform 1 protein. In another embodiment the means for detecting an isoform 1 gene product of the NF2 gene is an antibody that detectably binds to the isoform 1 gene product of the NF2 gene, optionally the isoform 1 gene product is merlin isoform 1 protein or neurofibromin-2 isoform 1 protein. In a further embodiment, the antibody that detectably binds to the isoform 1 gene product of the NF2 gene (such as merlin isoform 1 protein) does not detectably bind to other gene product isoforms, e.g. an isoform 2 gene product of the NF2 gene (such as merlin isoform 2 protein).

Definitions

The term "wild type" as is understood in the art refers to a polypeptide or polynucleotide sequence that occurs in a native population without genetic modification or a state of diploidy for a given genetic locus (2n). A deviation from diploid where a patient has three or more copies of a gene is considered 'amplified'. As is also understood in the art, a "variant" includes a polypeptide or polynucleotide sequence having at least one modification to an amino acid or nucleic acid compared to the corresponding amino acid or nucleic acid found in a wild type polypeptide or polynucleotide, respectively. Included in the term variant is Single Nucleotide Polymorphism (SNP) where a single base pair distinction exists in the sequence of a nucleic acid strand compared to the most prevalently found (wild type) nucleic acid strand. As used herein "genetic modification" or "genetically modified" refers to, but is not limited to, any suppression, substitution, amplification, deletion and/or insertion of one or more bases into DNA sequence(s). Also, as used herein "genetically modified" can refer to a gene encoding a polypeptide or a polypeptide having at least one deletion, substitution or suppression of a nucleic acid or amino acid, respectively. Alternative splicing (or differential splicing) is a process by which the exons of the RNA produced by transcription of a gene (a primary gene transcript or pre-mRNA) are reconnected in multiple ways during RNA splicing. The resulting different mRNAs may be translated into different protein isoforms; thus, a single gene may code for multiple proteins. Splicing variants are active mRNAs that result from alternative splicing.

Genetic variants and/or SNPs can be identified by known methods. For example, wild type or SNPs can be identified by DNA amplification and sequencing techniques, DNA and RNA detection techniques, including, but not limited to Northern and Southern blot, respectively, and/or various biochip and array technologies. WT and mutant polypeptides can be detected by a variety of techniques including, but not limited to immunodiagnostic techniques such as ELISA and western Blot. DNA amplifications in tumor cells can be identified by quantitative DNA detection techniques such as PCR based methods. In addition, microarray based methods can be used to measure DNA amplifications. These include microarray based comparative genomic hybridization (Greshock, J., et al. 2004. *Genome Res* 14: 179-87.) and DNA 'SNP Chips' (Bignell, G. R., et al. 2004 *Genome Res* 14: 287-95).

As used herein, the process of detecting an allele or polymorphism includes but is not limited to serologic and genetic methods. The allele or polymorphism detected may be functionally involved in affecting an individual's phenotype, or it may be an allele or polymorphism that is in linkage disequilibrium with a functional polymorphism/allele. Polymorphisms/alleles are evidenced in the genomic DNA of a subject, but may also be detectable from RNA, cDNA or protein sequences transcribed or translated from this region, as will be apparent to one skilled in the art.

As is well known genetics, nucleotide and related amino acid sequences obtained from different sources for the same gene may vary both in the numbering scheme and in the precise sequence. Such differences may be due to numbering schemes, inherent sequence variability within the gene, and/or to sequencing errors. Accordingly, reference herein to a particular polymorphic site by number will be understood by those of skill in the art to include those polymorphic sites that correspond in sequence and location within the gene, even where different numbering/nomenclature schemes are used to describe them.

As used herein, "genotyping" a subject (or DNA or other biological sample) for a polymorphic allele of a gene(s) or a mutation in at least one polypeptide or gene encoding at least one polypeptide means detecting which mutated, allelic or polymorphic form(s) of the gene(s) or gene expression products (e.g., hnRNA, mRNA or protein) are present or absent in a subject (or a sample). Related RNA or protein expressed from such gene may also be used to detect mutant or polymorphic variation. As is well known in the art, an individual may be heterozygous or homozygous for a particular allele. More than two allelic forms may exist, thus there may be more than three possible genotypes. As used herein, an allele may be 'detected' when other possible allelic variants have been ruled out; e.g., where a specified nucleic acid position is found to be neither adenine (A), thymine (T) or cytosine (C), it can be concluded that guanine (G) is present at that position (i.e., G is 'detected' or 'diagnosed' in a subject). Sequence variations may be detected directly (by, e.g., sequencing) or indirectly (e.g., by restriction fragment length polymorphism analysis, or detection of the hybridization of a probe of known sequence, or reference strand conformation polymorphism), or by using other known methods.

As used herein, a "genetic subset" of a population consists of those members of the population having a particular genotype or a tumor having at least one somatic mutation. In the case of a biallelic polymorphism, a population can potentially be divided into three subsets: homozygous for allele 1 (1,1), heterozygous (1,2), and homozygous for allele 2 (2,2). A 'population' of subjects may be defined using various criteria, e.g., individuals being treated with Compound A or individuals with cancer. In some instances, a genetic subset of a population may have a higher likelihood of response to treatment compared with another genetic subset. By way of another example, patients with a particular genotype may demonstrate an increased risk or decreased risk of a particular phenotypic response. In some embodiments of the methods herein, a subset of cancer patients with a deletion of all or part of the NF2 gene have a better response to treatment with Compound A (e.g., because that deletion is also found in the tumor that responds to Compound A, wherein the tumor cells, or a percentage of the tumor cells, do not have detectable amounts of a neurofibromin-2 isoform 1 because of the deletion of all or part of the NF2 gene).

As used herein, a subject that is "predisposed to" or "at increased risk of" a particular phenotypic response based on genotyping will be more likely to display that phenotype than an individual with a different genotype at the target polymorphic locus (or loci). Where the phenotypic response is based on a multi-allelic polymorphism, or on the genotyping of more than one gene, the relative risk may differ among the multiple possible genotypes.

As used herein "response" to treatment and grammatical variations thereof, includes but is not limited to an improved clinical condition of a patient after the patient received medication. Response can also mean that a patient's condition does not worsen upon start of treatment. Response can be defined by the measurement of certain manifestations of a disease or disorder. With respect to cancer, response can mean, but is not limited to, a reduction of the size and or number of tumors and/or tumor cells in a patient. Response can also be defined by other endpoints such as a reduction or attenuation in the number of pre-tumorous cells in a patient, or lack of disease progression, often referred to as "stable disease" or "time to progression of disease."

"Genetic testing" (also called genetic screening) as used herein refers to the testing of a biological sample from a subject to determine the subject's genotype; and may be utilized to determine if the subject's genotype comprises alleles that either cause, or increase susceptibility to, a particular phenotype (or that are in linkage disequilibrium with allele(s) causing or increasing susceptibility to that phenotype).

Biological samples for testing of one or more mutations may be selected from cancer or normal tissue, and include but not limited to a group of proteins, nucleotides, cellular blebs or components, serum, cells, blood, blood components such as circulating tumor DNA, urine and saliva. Samples may be tissue biopsies. Testing for mutations may be conducted by several techniques known in the art and/or described herein.

The sequence of any nucleic acid including a gene or PCR product or a fragment or portion thereof may be sequenced by any method known in the art (e.g., chemical sequencing or enzymatic sequencing). "Chemical sequencing" of DNA may denote methods such as that of Maxam and Gilbert (1977) (Proc. Natl. Acad. Sci. USA 74:560), in which DNA is randomly cleaved using individual base-specific reactions. "Enzymatic sequencing" of DNA may denote methods such as that of Sanger (Sanger, et al., (1977) Proc. Natl. Acad. Sci. USA 74:5463).

Conventional molecular biology, microbiology, and recombinant DNA techniques including sequencing techniques are well known among those skilled in the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook, et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel, et al. (eds.), Current Protocols in Molecular Biology, John Wiley & Sons, Inc. (1994

The Peptide Nucleic Acid (PNA) affinity assay is a derivative of traditional hybridization assays (Nielsen et al., Science 254:1497-1500 (1991); Egholm et al., J. Am. Chem. Soc. 114:1895-1897 (1992); James et al., Protein Science 3:1347-1350 (1994)). PNAs are structural DNA mimics that follow Watson-Crick base pairing rules, and are used in standard DNA hybridization assays. PNAs display greater specificity in hybridization assays because a PNA/DNA mismatch is more destabilizing than a DNA/DNA mismatch and complementary PNA/DNA strands form stronger bonds than complementary DNA/DNA strands.

DNA microarrays have been developed to detect genetic variations, polymorphisms, and cytogenetic alterations (e.g. DNA amplifications and deletions) (Taton et al., Science 289: 1757-60, 2000; Lockhart et al., Nature 405:827-836 (2000); Gerhold et al., Trends in Biochemical Sciences 24:168-73 (1999); Wallace, R. W., Molecular Medicine Today 3:384-89 (1997); Blanchard and Hood, Nature Biotechnology 149:1649 (1996); (Greshock, J., et al. 2004. Genome Res 14: 179-87; Bignell, G. R., et al. 2004 Genome Res 14: 287-95).). DNA microarrays are fabricated by high-speed robotics, on glass or nylon substrates, and contain DNA fragments with known identities ("the probe"). The microarrays are used for matching known and unknown DNA fragments ("the target") based on traditional base-pairing rules.

The terms "polypeptide" and "protein" are used interchangeably and are used herein as a generic term to refer to native protein, fragments, peptides, or analogs of a polypeptide sequence. Hence, native protein, fragments, and analogs are species of the polypeptide genus.

The terminology "X#Y" in the context of a mutation in a polypeptide sequence is art-recognized, where "#" indicates the location of the mutation in terms of the amino acid number of the polypeptide, "X" indicates the amino acid found at that position in the wild-type amino acid sequence, and "Y" indicates the mutant amino acid at that position. For example, the notation "G12S" with reference to the K-ras polypeptide indicates that there is a glycine at amino acid number 12 of the wild-type K-ras sequence, and that glycine is replaced with a serine in the mutant K-ras sequence.

The term "at least one mutation", or an analogous term thereof, in a polypeptide or a gene encoding a polypeptide and grammatical variations thereof means a polypeptide or gene encoding a polypeptide having one or more allelic variants, splice variants, derivative variants, substitution variants, deletion variants, and/or insertion variants, fusion polypeptides, orthologs, and/or interspecies homologs. By way of example, at least one mutation of NF2 would include an NF2 in which part of, or all of the sequence of a polypeptide (eg, merlin isoform 1 protein) or gene encoding the polypeptide is absent or not expressed in the cell for at least one of the merlin isoform 1 proteins produced in the cell. For example, a NF2 protein gene product (merlin protein, including merlin isoform 1 protein) may be produced by a cell in a truncated form and the sequence of the truncated form may be wild type over the sequence of the truncate. A deletion may mean the absence of all or part of a gene or protein encoded by a gene. Additionally, some of a protein expressed in or encoded by a cell may be mutated while other copies of the same protein produced in the same cell may be wild type. When a patient's cancer has at least one form of certain mutation, the person's cancer would be considered to have that mutation. Furthermore, as used herein, an NF2 mutation would include complete loss of all genes and parts of genes encoding merlin isoforms, such as merlin isoform 1, including by way of deletion, partial chromosome loss or chromosome loss. Alternatively, an NF2 mutation includes mutations or deletion in any regulatory elements necessary to translate or transcribe the NF2 gene, such that the mutation or deletion results in lack of transcription or translation of the NF2 gene. Thus, an NF2 mutation includes mutations or deletions in any regulatory elements necessary to translate or transcribe the NF2 gene, such that the mutation or deletion results in the lack of expression of isoform 1 in a cell, e.g. a tumor cell. Furthermore, mutation would include any insertion of genetic material that could disrupt the expression of NF2 gene products, such as merlin isoform 1, in a cell.

As used herein "genetic abnormality" is meant a deletion, substitution, addition, translocation, amplification and the like relative to the normal native nucleic acid content of a cell of a subject. The terms "mutant NF2" refers to the NF2 gene having at least one mutation. Certain exemplary NF2 mutant polypeptides include, but are not limited to, allelic variants, splice variants, derivative variants, substitution variants, deletion variants, and/or insertion variants, fusion polypeptides, orthologs, and interspecies homologs. In certain embodiments, mutant NF2 polypeptides include additional residues at the C- or N-terminus, such as, but not limited to, leader sequence residues, targeting residues, amino terminal methionine residues, lysine residues, tag residues and/or fusion protein residues.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes, although oligonucleotides may be double stranded, e.g. for use in the construction of a gene mutant. Oligonucleotides can be either sense or antisense oligonucleotides.

An oligonucleotide probe, or probe, is a nucleic acid molecule which typically ranges in size from about 8 nucleotides to several hundred nucleotides in length. Such a molecule is typically used to identify a target nucleic acid sequence in a sample by hybridizing to such target nucleic acid sequence under stringent hybridization conditions. Hybridization conditions have been described in detail above.

PCR primers are also nucleic acid sequences, although PCR primers are typically oligonucleotides of fairly short length which are used in polymerase chain reactions. PCR primers and hybridization probes can readily be developed and produced by those of skill in the art, using sequence information from the target sequence. (See, for example, Sambrook et al., supra or Glick et al., supra).

As used herein the term "amplification" and grammatical variations thereof refers to the presence of one or more extra gene copies in a chromosome complement. In certain embodiments a gene encoding a Ras protein may be amplified in a cell. Amplification of the HER2 gene has been correlated with certain types of cancer. Amplification of the HER2 gene has been found in human salivary gland and gastric tumor-derived cell lines, gastric and colon adenocarcinomas, and mammary gland adenocarcinomas. Semba et al., Proc. Natl. Acad. Sci. USA, 82:6497-6501 (1985); Yokota et al., Oncogene, 2:283-287 (1988); Zhou et al., Cancer Res., 47:6123-6125 (1987); King et al., Science, 229:974-976 (1985); Kraus et al., EMBO J., 6:605-610 (1987); van de Vijver et al., Mol. Cell. Biol., 7:2019-2023 (1987); Yamamoto et al., Nature, 319:230-234 (1986).

As used herein "overexpressed" and "overexpression" of a protein or polypeptide and grammatical variations thereof means that a given cell produces an increased number of a certain protein relative to a normal cell. By way of example, a protein may be overexpressed by a tumor cell relative to a non-tumor cell. Additionally, a mutant protein may be overexpressed compared to wild type protein in a cell. As is understood in the art, expression levels of a polypeptide in a cell can be normalized to a housekeeping gene such as actin. In some instances, a certain polypeptide may be underexpressed in a tumor cell compared with a non-tumor cell.

As used herein "nucleic acid necessary for expression of at least one gene product" refers to a nucleic acid sequence that encodes any portion of a gene and/or is operably linked to a nucleic acid encoding a gene product but does not necessarily comprise encoding sequence. By way of example, a nucleic acid sequence necessary for the expression of at least one gene product includes, but is not limited to, enhancers, promoters, regulatory sequences, start codons, stop codons, polyadenylation sequences, and/or encoding sequences. Expression levels of a polypeptide in a particular cell can be effected by, but not limited to, mutations, deletions and/or substitutions of various regulatory elements and/or non-encoding sequence in the cell genome.

As used herein, "treatment" means any manner in which one or more symptoms associated with the disorder are beneficially altered. Accordingly, the term includes healing or amelioration of a symptom or side effect of the disorder or a decrease in the rate of advancement of the disorder. Treatment also includes lengthening the time of progression free survival, e.g. as compared to progression free survival in untreated humans. Treatment also includes lengthening the time of progression free survival in FAK inhibitor treated humans with tumors with the absence a detectable amount of merlin isoform 1 protein as compared to FAK inhibitor treated humans with tumors which have a detectable amount of merlin isoform 1 protein. In certain embodiments of the methods of treating cancer herein, treatment means obtaining a clinically significant improvement in one or more symptoms, which can optionally be measured by RECIST criteria. In other embodiments, treatment means obtaining a statistically significant improvement in one or more symptoms, which can optionally be measured by RECIST criteria. In certain embodiments of the methods of treating cancer herein, wherein improvement in one or more symptoms is measured by RECIST criteria, the RECIST criteria are RECIST 1.1 criteria.

As used herein, the terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient. Tumors may be hematopoietic tumor, for example, tumors of blood cells or the like. Specific examples of clinical conditions based on such a tumor include leukemia such as chronic myelocytic leukemia or acute myelocytic leukemia; myeloma such as multiple myeloma; lymphoma and the like.

As is understood in the art, the terms "complete remission," "complete response" and "complete regression" mean the disappearance of all detectable signs and/or symptoms of cancer in response to treatment. As is also understood in the art detectable signs or symptoms of cancer can be defined based on the type and stage of cancer being treated. By way of example, "complete response" to treatment in a subject suffering from HCC could be defined as no visible liver tumors observed with X-ray or CT scan. In some instances, clinical response can be defined by RECIST 1.1 criteria (Eisenhauer EA, Therasse P, Bogaerts J, et al. New response evaluation criteria in solid tumours: Revised RECIST guideline (version 1.1). Eur J Cancer 2009; 45:228-247) as described briefly below:

RECIST 1.1 Criteria

Evaluation of Target Lesions

Definitions for assessment of response for target lesion(s) are as follows:

Complete Response (CR): Disappearance of all target lesions. Any pathological lymph nodes must be <10 mm in the short axis.

Partial Response (PR): At least a 30% decrease in the sum of the diameters of target lesions, taking as a reference, the baseline sum of the diameters (e.g. percent change from baseline).

Stable Disease Neither sufficient shrinkage to qualify for PR nor sufficient increase to qualify for progressive disease.

Progressive Disease (PD): At least a 20% increase in the sum of the diameters of target lesions, taking as a reference, the smallest sum of diameters recorded since the treatment started (e.g. percent change from nadir, where nadir is defined as the smallest sum of diameters recorded since treatment start). In addition, the sum must have an absolute increase from nadir of 5 mm.

Not Applicable (NA): No target lesions at baseline.

Not Evaluable (NE): Cannot be classified by one of the five preceding definitions.

Evaluation of Non-Target Lesions

Definitions for assessment of response for non-target lesions are as follows:

Complete Response (CR): The disappearance of all non-target lesions. All lymph nodes identified as a site of disease at baseline must be non-pathological (e.g. <10 mm short axis).

Non-CR/Non-PD: The persistence of 1 or more non-target lesion(s) or lymph nodes identified as a site of disease at baseline 0 mm short axis.

Progressive Disease (PD): Unequivocal progression of existing non-target lesions.

Not Applicable (NA): No non-target lesions at baseline.

Not Evaluable (NE): Cannot be classified by one of the four preceding definitions.

New Lesions

New malignancies denoting disease progression must be unequivocal. Lesions identified in follow-up in an anatomical location not scanned at baseline are considered new lesions. Any equivocal new lesions should continue to be followed. Treatment can continue at the discretion of the investigator until the next scheduled assessment. If at the next assessment the new lesion is considered to be unequivocal, progression should be documented.

Evaluation of Overall Response

The table below presents the overall response at an individual time point for all possible combinations of tumor responses in target and non-target lesions with or without the appearance of new lesions for subjects with measurable disease at baseline.

Evaluation of Overall Response for Subjects with Measurable Disease at Baseline in RECIST 1.1

| Target Lesions | Non-Target Lesions | New Lesions | Overall Response |
|---|---|---|---|
| CR | CR or NA | No | CR |
| CR | Non-CR/Non-PD or NE | No | PR |
| PR | Non-PD or NA or NE | No | PR |
| Stable disease | Non-PD or NA or NE | No | SD |
| NE | Non-PD or NA or NE | No | NE |
| PD | Any | Yes or No | PD |
| Any | PD | Yes or No | PD |
| Any | Any | Yes | PD |

CR = complete response, PR = partial response, PD = progressive disease, NA = not applicable, and NE = not evaluable RECIST 1.0 Criteria Definition of Measurable and Non-Measurable Disease Measurable Disease:

The presence of at least one measurable lesion.

Measurable Lesion:

Lesions that can be accurately measured in at least one dimension, with the longest diameter (LD) being:

≥20 mm with conventional techniques (medical photograph [skin or oral lesion], palpation, plain X-ray, CT, or MRI),

OR

≥10 mm with spiral CT scan.

Non-Measurable Lesion:

All other lesions including lesions too small to be considered measurable (longest diameter<20 mm with conventional techniques or <10 mm with spiral CT scan) including bone lesions, leptomeningeal disease, ascites, pleural or pericardial effusions, lymphangitis cutis/pulmonis, abdominal masses not confirmed and followed by imaging techniques, cystic lesions, or disease documented by indirect evidence only (e.g., by lab values).

Methods of Measurement

Conventional CT and MRI:

Minimum sized lesion should be twice the reconstruction interval. The minimum size of a baseline lesion may be 20 mm, provided the images are reconstructed contiguously at a minimum of 10 mm. MRI is preferred, and when used, lesions must be measured in the same anatomic plane by use of the same imaging sequences on subsequent examinations. Whenever possible, the same scanner should be used.

Spiral CT:

Minimum size of a baseline lesion may be 10 mm, provided the images are reconstructed contiguously at 5 mm intervals. This specification applies to the tumors of the chest, abdomen, and pelvis.

Chest X-Ray:

Lesions on chest X-ray are acceptable as measurable lesions when they are clearly defined and surrounded by aerated lung. However, MRI is preferable.

Clinical Examination:

Clinically detected lesions will only be considered measurable by RECIST criteria when they are superficial (e.g., skin nodules and palpable lymph nodes). In the case of skin lesions, documentation by color photography—including a ruler and patient study number in the field of view to estimate the size of the lesion—is required.

Baseline Documentation of Target and Non-Target Lesions

All measurable lesions up to a maximum of five lesions per organ and ten lesions in total, representative of all involved organs, should be identified as target lesions and recorded and measured at baseline.

Target lesions should be selected on the basis of their size (lesions with the LD) and their suitability for accurate repeated measurements (either clinically or by imaging techniques).

A sum of the LD for all target lesions will be calculated and reported as the baseline sum LD. The baseline sum LD will be used as a reference by which to characterize the objective tumor response.

All other lesions (or sites of disease) should be identified as non-target lesions and should also be recorded at baseline. Measurements of these lesions are not required, but the presence or absence of each should be noted throughout follow-up.

Documentation of indicator lesion(s) should include date of assessment, description of lesion site, dimensions, and type of diagnostic study used to follow lesion(s).

All measurements should be taken and recorded in metric notation, using a ruler or callipers.

Response Criteria

Disease assessments are to be performed every 6 weeks after initiating treatment. However, subjects experiencing a partial or complete response must have a confirmatory disease assessment at least 28 days later. Assessment should be performed as close to 28 days later (as scheduling allows), but no earlier than 28 days.

Definitions for assessment of response for target lesion(s) are as follows:

Evaluation of Target Lesions

Complete Response (CR)—disappearance of all target lesions.

Partial Response (PR)—at least a 30% decrease in the sum of the LD of target lesions, taking as a reference, the baseline sum LD.

Stable Disease (SD)—neither sufficient shrinkage to qualify for PR nor sufficient increase to qualify for progressive disease (PD), taking as a reference, the smallest sum LD since the treatment started. Lesions, taking as a reference, the smallest sum LD recorded since the treatment started or the appearance of one or more new lesions.

Evaluation of Non-Target Lesions

Definitions of the criteria used to determine the objective tumor response for non-target lesions are as follows:

Complete Response—the disappearance of all non-target lesions.

Incomplete Response/Stable Disease—the persistence of one or more non-target lesion(s).

Progressive Disease—the appearance of one or more new lesions and/or unequivocal progression of existing non-target lesions.

Evaluation of Overall Response for RECIST-Based Response

The overall response is the best response recorded from the start of the treatment until disease progression/recurrence is documented. In general, the subject's best response assignment will depend on the achievement of both measurement and confirmation criteria.

The following table presents the evaluation of best overall response for all possible combinations of tumor responses in target and non-target lesions with or without the appearance of new lesions.

| Target Lesion | Non-Target Lesion | New Lesion | Overall response |
|---|---|---|---|
| CR | CR | No | CR |
| CR | Incomplete response/(SD) | No | PR |
| PR | Non-PD | No | PR |
| SD | Non-PD | No | SD |
| PD | Any | Yes or No | PD |
| Any | PD | Yes of No | PD |
| Any | Any | Yes | PD |

Note:

Subjects with a global deterioration of health status requiring discontinuation of treatment without objective evidence of disease progression at that time should be classified as having "symptomatic deterioration". Every effort should be made to document the objective progression even after discontinuation of treatment.

In some circumstances, it may be difficult to distinguish residual disease from normal tissue. When the evaluation of complete response depends on this determination, it is recommended that the residual lesion be investigated (fine needle aspirate/biopsy) to confirm the complete response status.

Combinations

When a FAK inhibitor such as, but not limited to, Compound A is administered for the treatment of cancer, the term "co-administering" and derivatives thereof as used herein is meant either simultaneous administration or any manner of separate sequential administration of a FAK inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. If the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice f Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present FAK inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside] is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside] is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I: DNA: irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

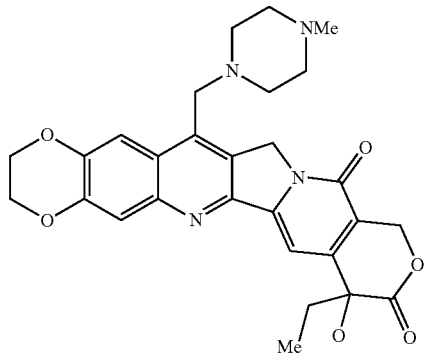

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Letrozole (trade name Femara) is an oral non-steroidal aromatase inhibitor for the treatment of hormonally-responsive breast cancer after surgery. Estrogens are produced by the conversion of androgens through the activity of the aromatase enzyme. Estrogens then bind to an estrogen receptor, which causes cells to divide. Letrozole prevents the aromatase from producing estrogens by competitive, reversible binding to the heme of its cytochrome P450 unit. The action is specific, and letrozole does not reduce production of mineralo- or corticosteroids.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases. Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by overexpression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, P13-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-lacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myo-inositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and Bennett, C. F. and Cowsert, L. M. BioChim. Biophys. Acta, (1999) 1489(1):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer: erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$, beta$_3$) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Pazopanib which commercially available as VOTRIENT® is a tyrosine kinase inhibitor (TKI). Pazopanib is presented as the hydrochloride salt, with the chemical name 5-[[4-[(2,3-dimethyl-2H-indazol-6-yl)methylamino]-2-pyrimidinyl]amino]-2-methylbenzenesulfonamide monohydrochloride. Pazoponib is approved for treatment of patients with advanced renal cell carcinoma.

Bevacisumab which is commercially available as AVASTIN® is a humanized monoclonal antibody that blocks VEGF-A. AVASTIN® is approved form the treatment of various cancers including colorectal, lung, breast, kidney, and glioblastomas.

mTOR inhibitors include but are not limited to rapamycin (FK506) and rapalogs, RAD001 or everolimus (Afinitor), CCI-779 or temsirolimus, AP23573, AZD8055, WYE-354, WYE-600, WYE-687 and Pp121.

Everolimus is sold as Afinitor® by Novartis and is the 40-O-(2-hydroxyethyl) derivative of sirolimus and works similarly to sirolimus as an mTOR (mammalian target of rapamycin) inhibitor. It is currently used as an immunosuppressant to prevent rejection of organ transplants and treatment of renal cell cancer. Much research has also been conducted on everolimus and other mTOR inhibitors for use in a number of cancers. It has the following chemical structure (formula II) and chemical name:

(II)

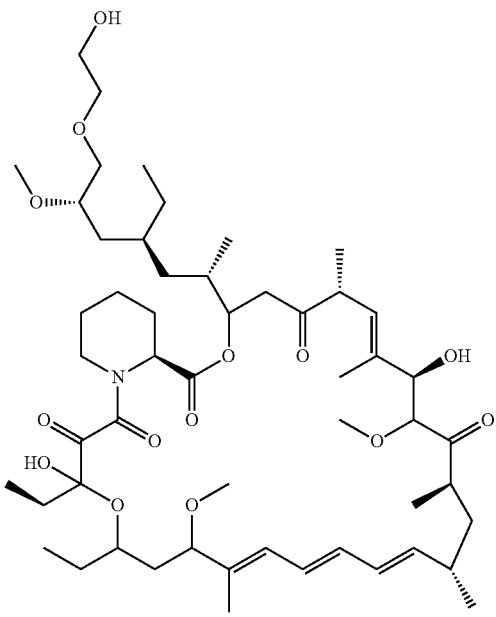

dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0$^{4,9}$]hexatriaconta-16,24,26,28-tetraene-2,3,10,14,20-pentone.

Bexarotene is sold as Targretin® and is a member of a subclass of retinoids that selectively activate retinoid X receptors (RXRs). These retinoid receptors have biologic activity distinct from that of retinoic acid receptors (RARs). The chemical name is 4-[1-(5,6,7,8-tetrahydro-3,5,5,8,8-pentamethyl-2-naphthalenyl)ethenyl]benzoic acid. Bexarotene is used to treat cutaneous T-cell lymphoma (CTCL, a type of skin cancer) in people whose disease could not be treated successfully with at least one other medication.

Sorafenib marketed as Nexavar® is in a class of medications called multikinase inhibitors. Its chemical name is 4-[4-[[4-chloro-3-(trifluoromethyl)phenyl]carbamoylamino]phenoxy]-N-methyl-pyridine-2-carboxamide. Sorafenib is used to treat advanced renal cell carcinoma (a type of cancer that begins in the kidneys). Sorafenib is also used to treat unresectable hepatocellular carcinoma (a type of liver cancer that cannot be treated with surgery).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Examples of erbB inhibitors include lapatinib, erlotinib, and gefitinib. Lapatinib, N-(3-chloro-4-{[(3-fluorophenyl)methyl]oxy}phenyl)-6-[5-({[2-(methylsulfonyl)ethyl]amino}methyl)-2-furanyl]-4-quinazolinamine (represented by Formula I, as illustrated), is a potent, oral, small-molecule, dual inhibitor of erbB-1 and erbB-2 (EGFR and HER2) tyrosine kinases that is approved in combination with capecitabine for the treatment of HER2-positive metastatic breast cancer.

I

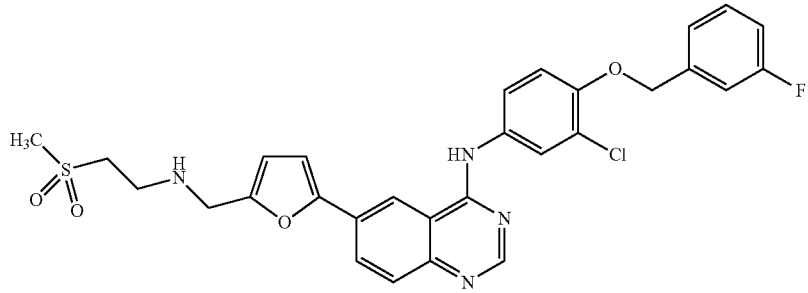

The free base, HCl salts, and ditosylate salts of the compound of formula (I) may be prepared according to the procedures disclosed in WO 99/35146, published Jul. 15, 1999; and WO 02/02552 published Jan. 10, 2002.

Erlotinib, N-(3-ethynylphenyl)-6,7-bis{[2-(methyloxy) ethyl]oxy}-4-quinazolinamine Commercially available under the tradename Tarceva) is represented by formula II, as illustrated:

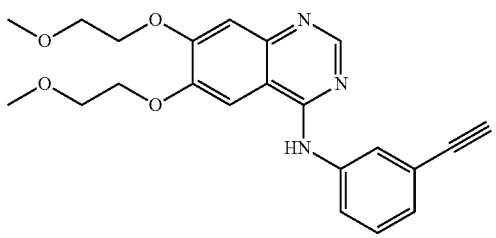

The free base and HCl salt of erlotinib may be prepared, for example, according to U.S. Pat. No. 5,747,498, Example 20.

Gefitinib, 4-quinazolinamine,N-(3-chloro-4-fluorophenyl)-7-methoxy-6-[3-4-morpholin)propoxy] is represented by formula III, as illustrated:

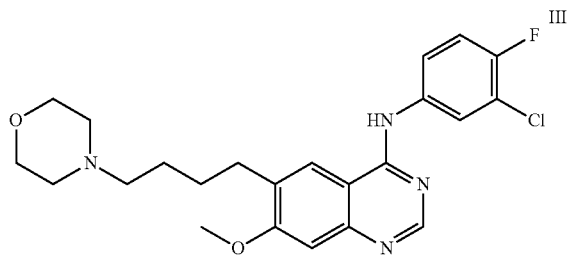 [SMILES: COc1cc2ncnc(Nc3ccc(F)c(Cl)c3)c2cc1CCCCN1CCOCC1]

Gefitinib, which is commercially available under the trade name IRESSA® (Astra-Zenenca) is an erbB-1 inhibitor that is indicated as monotherapy for the treatment of patients with locally advanced or metastatic non-small-cell lung cancer after failure of both platinum-based and docetaxel chemotherapies. The free base, HCl salts, and diHCl salts of gefitinib may be prepared according to the procedures of International Patent Application No. PCT/GB96/00961, filed Apr. 23, 1996, and published as WO 96/33980 on Oct. 31, 1996.

Trastuzumab (HEREPTIN®) is a humanized monoclonal antibody that binds to the HER2 receptor. It original indication is HER2 positive breast cancer.

Cetuximab (ERBITUX®) is a chimeric mouse human antibody that inhibits epidermal growth factor receptor (EGFR).

Pertuzumab (also called 2C4, trade name Omnitarg) is a monoclonal antibody. The first of its class in a line of agents called "HER dimerization inhibitors". By binding to HER2, it inhibits the dimerization of HER2 with other HER receptors, which is hypothesized to result in slowed tumor growth. Pertuzumab is described in WO01/00245 published Jan. 4, 2001.

Rituximab is a chimeric monoclonal antibody which is sold as RITUXAN® and MABTHERA@. Rituximab binds to CD20 on B cells and causes cell apoptosis. Rituximab is administered intravenously and is approved for treatment of rheumatoid arthritis and B-cell non-Hodgkin's lymphoma.

Ofatumumab is a fully human monoclonal antibody which is sold as ARZERRA®. Ofatumumab binds to CD20 on B cells and is used to treat chronic lymphocytic leukemia (CLL; a type of cancer of the white blood cells) in adults who are refractory to treatment with fludarabine (Fludara) and alemtuzumab (Campath).

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signaling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes determining the presence or absence of a detectable amount of a gene product of the Neurofibromin-2 (NF2) gene in a sample from said human, and administering to said human an effective amount of a focal adhesion kinase (FAK) inhibitor, or a pharmaceutically acceptable salt thereof, if no gene product or no isoform 1 gene product is detected and the co-administration of at least one anti-neoplastic agent with said FAK inhibitor. By way of example, the invention provides method of treating cancer in a human in need thereof comprising determining the presence or absence of a detectable amount of merlin or a functional fragment thereof from a tumor sample from said human, and administering to said human an effective amount of 2-[(5-chloro-2-{[3-methyl-1-(1-methylethyl)-1H-pyrazol-5-yl]amino}-4-pyridinyl)amino]-N-(methyloxy)benzamide, or a pharmaceutically acceptable salt thereof, and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors if no merlin or functional fragment thereof is detected.

Pharmaceutical Compositions

While it is possible that, the compound of formula (I), as well as pharmaceutically acceptable salts and solvates thereof, may be administered as the raw chemical, it is also possible to present the active ingredient as a pharmaceutical composition. Accordingly, embodiments of the invention further provide pharmaceutical compositions, which include therapeutically effective amounts of Compound A, and one or more pharmaceutically acceptable carriers, diluents, or excipients. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing Compound A with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 3.5 g, preferably 1 mg to 1500 mg, 1 to 3 times a day, of a compound of the formula (I) depending on the condition being treated, the route of administration and the age, weight and condition of the patient. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art. In one embodiment, the human is administered between about 80 mg to about 1500 mg twice a day (BID) of FAK inhibitor. In another embodiment, the human is administered between about 300 mg to about 1500 mg twice a day (BID) of FAK inhibitor. In another embodiment, the human is administered between about 300 mg to about 1000 mg twice a day (BID) of FAK inhibitor. In another embodiment, the human is administered 50, 80, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500 mg twice a day (BID) of FAK inhibitor.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

Dosage unit forms can also be in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of formula (I) or a pharmaceutically acceptable salt or solvate thereof will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) or a salt or solvate thereof for the treatment of a cancerous condition such as those described herein will generally be in the range of 0.1 to 100 mg/kg body weight of recipient (mammal) per day and more usually in the range of 1 to 50 mg/kg body weight per day. Thus, for a 70 kg adult mammal, the actual amount per day would usually be from 7 to 3500 mg and this amount may be given in a single dose per day or more usually in a number (such as two, three, four, five or six) of sub-doses per day such that the total daily dose is the same. An effective amount of a salt or solvate thereof may be determined as a proportion of the effective amount of the compound of formula (I) per se. It is envisaged that similar dosages would be appropriate for treatment of the other conditions referred to above.

The amount of administered or prescribed compound according to these aspects of the present invention will depend upon a number of factors including, for example, the age and weight of the patient, the precise condition requiring treatment, the severity of the condition, comorbid conditions, hepatic or renal function, the nature of the formulation, and the route of administration. Ultimately, the amount will be at the discretion of the attendant physician.

EXAMPLES

The following examples are intended for illustration only and are not intended to limit the scope of the invention in any way. Each reference cited in the Examples is incorporated by reference in its entirety.

Example 1

Preparation of Compound A

Compound A can be prepared according to the disclosure of International Publication Number WO2010/062578, and by the methods shown below.

Small Scale Preparation of Compound A

2-[(5-Chloro-2-{[3-methyl-1-(1-methylethyl)-1H-pyrazol-5-yl]amino}-4-pyridinyl)amino]-N-(methyloxy)benzamide

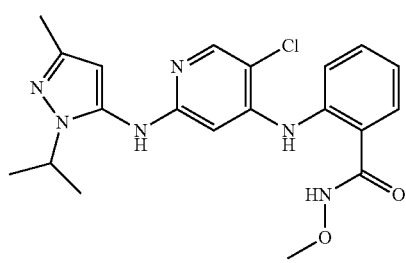 [SMILES: CONC(=O)c1ccccc1Nc1cc(Nc2cc(C)nn2C(C)C)ncc1Cl]

A microwave tube was charged with 2-[(2,5-dichloro-4-pyridinyl)amino]-N-(methyloxy)benzamide (70 mg, 0.224 mmol), {3-methyl-1-(1-methylethyl)-1H-pyrazol-5-amine (70 mg, 0.503 mmol) and cesium carbonate (230 mg, 0.706 mmol). The reaction mixture was degassed with nitrogen for 10 min. At same time, BINAP (50 mg, 0.080 mmol) and palladium(II) acetate (10 mg, 0.045 mmol) were added. The reaction mixture was heated in a microwave at 160° C. for 40 min. The crude material was purified on reverse-phase HPLC (Gilson) eluting with $CH_3CN/H_2O$ with 0.1% formic acid which gave a title compound (15 mg, 15%); MS: $M(C_{20}H_{23}ClN_6O_2)$=414.89, $(M+H)^+$=415, 416; 1H NMR (400 MHz, CHLOROFORM-d) δ ppm 9.42 (br. s., 1H) 8.71 (br. s., 1H) 8.02 (s, 1H) 7.54 (br. s., 1H) 7.06 (t, J=7.5 Hz, 1H) 6.48 (s, 1H) 6.32 (br. s., 1H) 5.86 (s, 1H) 4.47 (dt, J=13.4, 6.7 Hz, 1H) 3.92 (s, 3H) 2.26 (s, 3H) 1.41-1.43 (d, J=6.6 Hz, 2H).

Large Scale Preparation of Compound A

Intermediate 1

2-[(2,5-Dichloro-4-pyridinyl)amino]benzonitrile

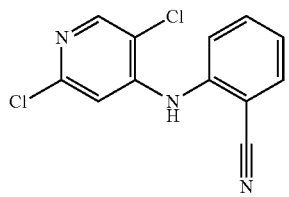 [SMILES: N#Cc1ccccc1Nc1cc(Cl)ncc1Cl]

The solution of 2,5-dichloro-4-iodopyridine (100 g, 365 mmol), 2-aminobenzonitrile (43.1 g, 365 mmol) and potassium triphosphate (233 g, 1095 mmol) in 1,4-dioxane (2.5 L) was degassed by $N_2$ stream. To this solution was added DPEPhos (15.73 g, 29.2 mmol) and palladium acetate (3.28 g, 14.60 mmol). The reaction mixture was stirred at reflux for 18 hour. The solution was filtered through 0.5 in. celite and 0.2 inch of silica. The solution was evaporated. Solid was suspended in the diethyl ether and filtered. Diethyl ether was concentrated, and the resulting solid was filtered. 2-[(2,5-Dichloro-4-pyridinyl)amino]benzonitrile (80 g, 288 mmol, 79% yield) was isolated as an orange solid. 1H NMR (400 MHz, DMSO-$d_6$) δ ppm 6.49 (s, 1H) 7.50 (td, J=7.58, 1.01 Hz, 1H) 7.56 (d, J=7.58 Hz, 1H) 7.80 (td, J=7.83, 1.77 Hz, 1H) 7.95 (dd, J=7.83, 1.52 Hz, 1H) 8.26 (s, 1H) 9.05 (brs, 1H); HPLC Rt=2.88 min, MS (ESI): 263.9, 265.9 $[M+H]^+$.

Intermediate 2

2-[(5-Chloro-2-{[3-methyl-1-(1-methylethyl)-1H-pyrazol-5-yl]amino}-4-pyridinyl)amino]benzonitrile

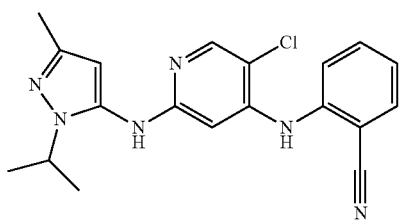 [SMILES: Cc1cc(Nc2cc(Nc3ccccc3C#N)c(Cl)cn2)n(C(C)C)n1]

The solution of 2-[(2,5-dichloro-4-pyridinyl)amino]benzonitrile (110 g, 396 mmol), 3-methyl-1-(1-methylethyl)-1H-pyrazol-5-amine (55.1 g, 396 mmol), and cesium carbonate (387 g, 1187 mmol) in 1,4-dioxane (2.5 L) was degassed by $N_2$ stream, and 2,2'-bis(diphenylphosphino)-1,1'-binaphthyl (BINAP) (19.71 g, 31.7 mmol) followed by palladium acetate (3.55 g, 15.83 mmol) were added. The reaction mixture was heated to reflux for overnight under $N_2$. The reaction mixture was filtered and the liquid was concentrated. Ethyl acetate (1500 mL), followed by 1 M HCl (1000 mL) were added. Layers were separated. Ethyl acetate was washed with 1 M HCl until no product was observed by HPLC (1000 mL total, 1×). HCl phases were combined, and backwashed with ethyl acetate (3×1000 mL), until the product peak was relativity pure in the HCL layer. The HCl layer was then basified with NaOH (50 w/w followed by 1 M) to ph~4 resulting in a cloudy solution. Ethyl acetate (2000 mL) was added and layers were separated. The ethyl acetate was washed with brine and evaporated. After neutralization—after addition of ethyl acetate—the reaction mixture was filtered to get some product. Also isolation of product during evaporation can be done by filtration of white solid, which comes from the mother liquor. All solids and evaporated products were combined. 2-[(5-Chloro-2-{[3-methyl-1-(1-methylethyl)-1H-pyrazol-5-yl]amino}-4-pyridinyl)amino]benzonitrile (80 g, 207 mmol, 52.4% yield) was isolated as a yellow solid. 1H NMR (400 MHz, DMSO-$d_6$) δ ppm 1.24 (d, J=6.57 Hz, 6H) 2.08 (s, 3H) 4.34 (quin, J=6.57 Hz, 1H) 5.87 (s, 1H) 5.97 (s, 1H) 7.41 (td, J=7.58, 1.01 Hz, 1H) 7.47 (d, J=8.08 Hz, 1H) 7.75 (td, J=7.83, 1.52 Hz, 1H) 7.90 (dd, J=7.83, 1.52 Hz, 1H) 7.94 (s, 1H) 8.42 (d, J=17.43 Hz, 2H); HPLC Rt=2.36 min, MS (ESI): [M+H]$^+$=367.1, 368.1.

Intermediate 3

2-[(5-Chloro-2-{[3-methyl-1-(1-methylethyl)-1H-pyrazol-5-yl]amino}-4-pyridinyl)amino]benzoic acid

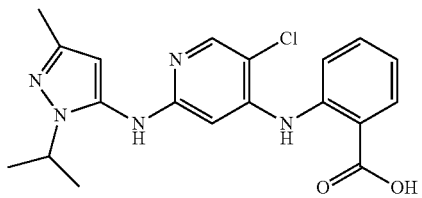 [SMILES: Cc1cc(Nc2cc(Nc3ccccc3C(=O)O)c(Cl)cn2)n(C(C)C)n1]

2-[(5-Chloro-2-{[3-methyl-1-(1-methylethyl)-1H-pyrazol-5-yl]amino}-4-pyridinyl)amino]benzonitrile (80 g, 218 mmol) was dissolved in 1,4-dioxane (1.5 L) and 1 M NaOH (1500 mL, 1500 mmol) was added. The suspension was refluxed overnight. After cooling to RT, ethyl acetate (1 L) was added and layers were separated. The water layer was washed with 1 L of ethyl acetate. Both organic layers were combined and backwashed with 0.1 M NaOH (1 L) until no product was observed in organic. The organics were then discarded. Combined aqueous were then washed with 1 L of ethyl acetate. The water layer was then acidified with acetic acid (very slowly to ph~7). The solid was filtered and 2-[(5-chloro-2-{[3-methyl-1-(1-methylethyl)-1H-pyrazol-5-yl]amino}-4-pyridinyl)amino]benzoic acid (67 g, 165 mmol, 76% yield) was isolated as a yellow solid. 1H NMR (400 MHz, DMSO-$d_6$) δ ppm 1.28 (d, J=6.57 Hz, 6H) 2.11 (s, 3H) 4.41 (quin, J=6.57 Hz, 1H) 5.96 (s, 1H) 6.83 (s, 1H) 7.09 (ddd, J=8.02, 5.12, 3.03 Hz, 1H) 7.40 (1H) 7.52-7.61 (m, 2H) 7.91-8.16 (m, 2H) 8.55 (s, 1H) 10.17 (brs, 1H) 13.64 (brs, 1H); HPLC Rt=2.35 min, MS (ESI): [M+H]$^+$=386.1.

2-[(5-Chloro-2-{[3-methyl-1-(1-methylethyl)-1H-pyrazol-5-yl]amino}-4-pyridinyl)amino]-N-(methyloxy)benzamide

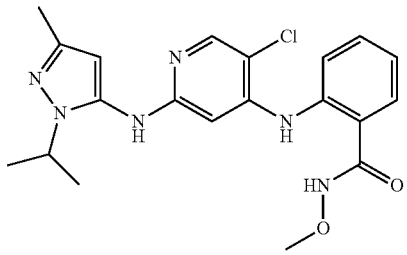 [SMILES: CONC(=O)c1ccccc1Nc1cc(Nc2cc(C)nn2C(C)C)ncc1Cl]

To a solution of 2-[(5-chloro-2-{[3-methyl-1-(1-methylethyl)-1H-pyrazol-5-yl]amino}-4-pyridinyl)amino]benzoic acid (67 g, 174 mmol) and 1-hydroxybenzotriazole (29.3 g, 191 mmol) in N,N-dimethylformamide (700 mL) was added N-(3-dimethylaminopropyl)-N'-ethylcarbodiimide (36.6 g, 191 mmol) and the solution was stirred for 30 minutes. O-Methylhydroxylamine hydrochloride (15.95 g, 191 mmol) was added and the solution stirred for additional 15 minutes, the cooled down to the 0° C. and diisopropylethlyamine (91 mL, 521 mmol) was added dropwise. The reaction mixture was stirred overnight tat the room temperature. Water (4000 mL) was added and the solution was acidified with acetic acid (20 mL). The solution was extracted 2×2 L of ethyl acetate. The organic was washed with water (1 L), brine, and dried over MgSO$_4$, filtered and evaporated. 2-[(5-Chloro-2-{[3-methyl-1-(1-methylethyl)-1H-pyrazol-5-yl]amino}-4-pyridinyl)amino]-N-(methyloxy)benzamide (74 g, 164 mmol, 94% yield, 92% pure) was isolated as a yellow foam. 1H NMR (400 MHz, DMSO-$d_6$) δ ppm 1.27 (d, J=6.57 Hz, 6H) 2.10 (s, 3H) 3.71 (s, 3H) 4.39 (quin, J=6.51 Hz, 1H) 5.93 (s, 1H) 6.66 (s, 1H) 7.08-7.19 (m, 1H) 7.49-7.64 (m, 3H) 7.98 (s, 1H) 8.50 (s, 1H) 9.50 (s, 1H) 11.93 (s, 1H).; HPLC Rt=2.13 min, MS (ESI): [M+H]$^+$=415.1.

Purification of Example 1 Products

2-[(5-Chloro-2-{[3-methyl-1-(1-methylethyl)-1H-pyrazol-5-yl]amino}-4-pyridinyl)amino]-N-(methyloxy)benzamide (173.3 g, 63.5% w/w, 265.2 mmoles) was dissolved in ethyl acetate (3.50 L, 20 volumes) and heated to about 50° C. To this solution was added Si-thiol (functionalized silica gel) (87 g, 50% loading). The mixture was held at about 50° C. for 16-20 hours. It was then filtered off the Si-thiol silica gel. The filter cake was rinsed with ethyl acetate (2×200 mL each) and filtrates were combined. Then the combined filtrates were washed with 1 M aqueous ammonium formate at pH 9.4 (5×1 L each), washed with water, brine, and dried over magnesium sulfate. Dried EtOAC was filtered and stripped to dryness giving a yellow foam. It was dried at 50-55° C. for about 2 hours to a constant weight of 160 g. This material was slurried in methylene chloride (800 mL, 5 volumes), heated to reflux to afford a solution, and filtered. The solution was cooled to 20-25° C. The product crystallized upon cooling. After about 2 hours, the product was collected by filtration and rinsed with methylene chloride. The white solid was dried at 50-55° C. for 14-16 hours to a constant weight. 2-[(5-Chloro-2-{[3-methyl-1-(1-methylethyl)-1H-pyrazol-5-yl]amino}-4-pyridinyl)amino]-N-(methyloxy)benzamide (85.0 g, 204.9 mmoles, 77% overall yield) was isolated as a white solid. 1H NMR (400 MHz, DMSO-$d_6$) δ ppm 1.27 (d, J=6.57 Hz, 6H) 2.10 (s, 3H) 3.70 (s, 3H) 4.39 (quin, J=6.57 Hz, 1H) 5.92 (s, 1H) 6.66 (s, 1H) 7.02-7.24 (m, 1H) 7.45-7.68 (m, 3H) 7.98 (s, 1H) 8.48 (s, 1H) 9.49 (br. s, 1H) 11.91 (s, 1H). C18 HPLC RT=6.2 minutes (99.0% purity). MS (ESI): 415.0 [M+H]$^+$.

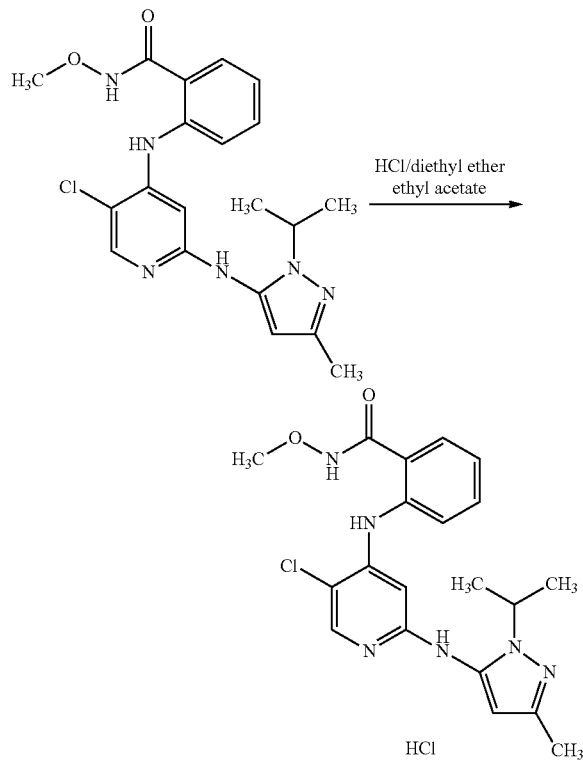

2-[(5-Chloro-2-{[3-methyl-1-(1-methylethyl)-1H-pyrazol-5-yl]amino}-4-pyridinyl)amino]-N-(methyloxy)benzamide (235.2 g total weight, 228.0 g assayed content, 549.5 mmoles) was slurried in ethyl acetate (7.1 L, 30 volumes). The mixture was heated to about 50-55° C. to afford a cloudy solution. The cloudy solution was filtered. To the filtered solution was added 2.0 M HCl in diethyl ether (210 g, 281 mL, 1.02 equiv.) over 15-20 minutes. Upon HCl addition, a white slurry was observed. It was stirred at room temperature for about 16-20 hours. Product was collected by filtration and rinsed with ethyl acetate (2×500 mL each). The wet cake was dried at 50-55° C./<5 mm Hg for 16-20 hours to a constant weight. 2-[(5-Chloro-2-{[3-methyl-1-(1-methylethyl)-1H-pyrazol-5-yl]amino}-4-pyridinyl)amino]-N-(methyloxy)benzamide, monohydrochloride, (245.9 g, 544.7 mmoles, 96% yield) was isolated as a white solid. 1H NMR (400 MHz, DMSO-$d_6$) δ ppm 1.32 (d, J=6.57 Hz, 6H) 2.18 (s, 3H) 3.70 (s, 3H) 4.35-4.62 (m, 1H) 6.12 (br. s, 1H) 6.60 (br. s, 1H) 7.19-7.41 (m, 1H) 7.48-7.75 (m, 3H) 8.09 (s, 1H) 9.59-9.99 (m, 2H) 11.98 (br. s, 1H). C18 HPLC RT=6.1 minutes (99.6% purity). MS (ESI): 414.8 [M+H]$^+$.

Biological Data

Example 2

Antibodies Used in Western Blots

Standard procedures for western blotting were used and the specific antibodies for these studies were: anti-FAK (Millipore #05-537), anti-pFAK (InVitrogen 44-624G), anti-merlin (Santa Cruz #28247), anti-merlin isoform 1 (Santa Cruz #332). Results are shown in FIG. 1.

Example 3

Human Cell Lines

Five human mesothelioma cell lines and two additional human lung cancer cell lines available from the ATCC were used in these studies. Cells were grown in RPMI1640 media containing 10% FBS, 1% L-glutamine, 1% sodium pyruvate under standard cell culture conditions. The mesothelioma cell lines: NCI-H2052, MSTO-211H, NCI-H28, NCI-H226, NCI-H2452, and additional lung lines: A549 and SW-1573. An additional three mesothelioma cell lines, Mero-41, Mero-82, and Mero-14, were grown under identical conditions.

Example 4

Anchorage-Independent Growth-Death Assay

The cellular response to Compound A was evaluated in an anchorage-independent cell growth assay that quantified the extent of cell growth inhibition and the net change in cell population. The assay was performed in black, clear bottom, untreated 384-well plates (Greiner #781096). It is important to use either non-tissue culture treated or Low Attachment plates to prevent cells from adhering to the plate during the assay. In brief, the assay was performed as described below.

A 1% (weight/volume) stock of methylcellulose solution was prepared by dissolving 5 grams of sterilized methylcellulose (Sigma #M0512) in 495 mL of cell culture medium. Here, RPMI1640 media containing 10% FBS, 1% L-glutamine, 1% sodium pyruvate was added to the cooled methylcellulose that had been placed in a glass container and autoclaved to sterilize. Media can be substituted if the cells require different cell culture medium for growth. The dissolution often took a day with vigorous stirring at 4° C. maintaining sterile conditions.

Cells were plated into a 384 well plate with assay conditions of 0.65% methylcellulose (final concentration) and 1000 cells per well in a final volume of 48 μL. This was achieved by diluting cells harvested from culture and re-suspended in growth medium (dilute to 2.0833×10$^4$ cells/mL) with the 1% methylcellulose. The cells were mixed by inversion to distribute evenly, bubbles were dispersed and 48 μL was placed into the well with a positive displacement pipette. The plates were placed in a cell culture incubator containing 5% $CO_2$ at 37° C.

Serial dilution of compound in DMSO was done in a 384 well plate starting with 20 μL of stock compound solution in the first column and 10 μL of DMSO in the other wells. Ten μL from the compound well was transferred into the DMSO containing well, mixed, and the serial dilution was continued with 10 μL transfers across the plate. Then, 4 μL of this DMSO diluted compound was added into wells of a new 384 well plate containing 105 μL of appropriate growth medium. This 'compound plate' was used to dose the assay plates containing cells in methylcellulose.

To initiate the assay, two μL from each well of the 'compound plate' were added to individual wells of the 'assay plates,' each well containing the 48 μL of cells in methylcellulose. These assay plates were placed in the cell culture incubator for 6 days. One plate was selected at random and developed with Cell TiterGlo (CTG) at the time of compound addition to represent the time equal zero (T0) plate, i.e. to represent the number of cells at the time of compound addition.

On day 6, the assay was stopped by developing the plates, placing a black sticker on bottom of each plate to block light, adding 25 μL of CTG, and incubating the plates for 20 minutes at room temperature. The plates were scanned using a luminescence protocol on the EnVision (Perkin-Elmer).

Results were expressed as a percent of the T0 value and plotted against the compound concentration. All values had a 'no cell' background subtraction and the T0 value was normalized to 100% and represents the number of cells at the time of compound addition. The cellular response was determined by fitting the concentration response curves using a 4-parameter curve fit equation and determining the concentration that inhibited growth by 50% ($gIC_{50}$). The $gIC_{50}$ value is the midpoint of the growth window (between T0 and growth of DMSO controls). The measure of net change in the population was quantified by the Ymin-T0 value that was determined by subtracting the T0 value (100%) from the Ymin value (%) that was determined from the fit of the concentration response curve.

Example 6

Expression of NF2 Tumor Suppressor Gene (Isoform 1 Protein Gene Product of the NF2 Gene, Also Called Neurofibromin-2 Isoform 1 Protein, Also Called Merlin Isoform 1 Protein)

The expression of the tumor suppressor isoform of the NF2 gene was evaluated in the mesothelioma cell lines by western blotting of whole cell lysates. The NF2 gene generates 2 major gene products, merlin isoform 1 protein composed of 595 amino acids and merlin isoform 2 protein composed of 590 amino acids. Using an antibody that detects both isoform 1 and 2, two prominent bands of the expected molecular weight, just under 75 kilodaltons (KD), were detected in 4 of the 7 cells analyzed (FIG. 1A). Three cell lines, NCI-H226, NCI-H2052, and SW1573 lacked the upper band of the doublet suggesting the longer (lower mobility) isoform 1 was not expressed. An antibody that specifically detects isoform 1 of merlin confirmed this observation (FIG. 1B). Results from the analysis of additional cells lines is shown in Table 3.

Example 7

Immunohistochemistry

Figure 3:
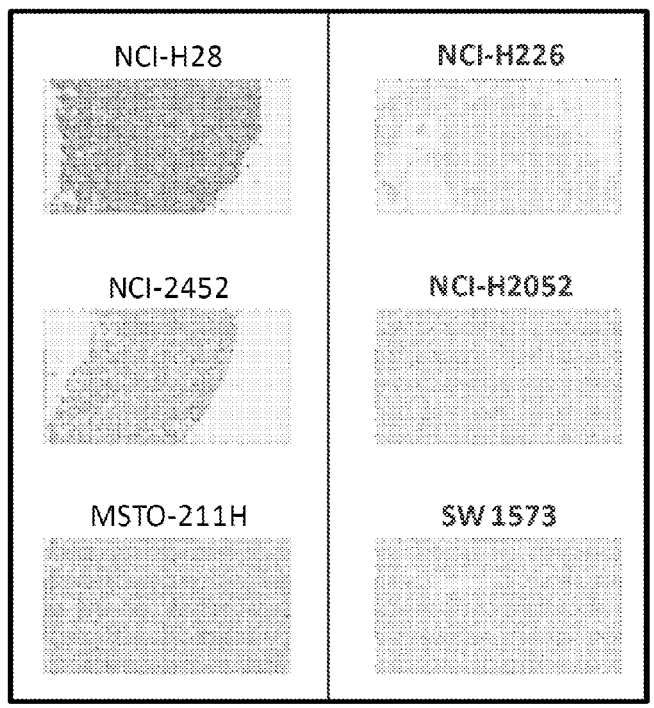
FIG. 3 shows images of immunohistochemical detection of the protein gene product of isoform 1 of NF2 (merlin isoform 1) in five mesothelioma cell lines and one lung cell line (cells in which merlin isoform 1 is not detected, left panel; cells in which merlin isoform 1 is detected, right panel).

Four mesothelioma cell lines and 1 lung cell line were evaluated by immunohistochemistry (IHC), as shown in FIG. 3. The IHC staining pattern for merlin isoform 1 was the same as seen in the western blots (See western blots in FIG. 1). Three cell lines (NCI-H226, NCI-H2052, and SW-1573) were negative for merlin isoform 1 staining (left panel) and 3 cell lines (NCI-H28, NCI-2452, and MSTO-211H) were positive for merlin isoform 1 staining (right panel).

Example 8

Evaluation of Genomic DNA Containing the NF2 Gene and Evaluation of mRNA Expression of Isoform 1 of the NF2 Gene, in Cell Lines Additional confirmation of the NF2 gene status was provided by sequencing the genomic DNA (gDNA) and mRNA (cDNA) from the cell lines. The sequencing results for the expressed form of the gene, the cDNA, were consistent with the gDNA as shown in Table 1. In addition, sequencing the expressed mRNA allowed the independent confirmation of the status of isoform 1 and isoform 2. The results from sequencing both cDNA and gDNA were consistent with the results from the western blots and IHC analysis. These different means of analysis led to the same classification of cell lines in regards to merlin status.

TABLE 1

Sequence analysis of the NF2 gene and expressed RNA products. Five human mesothelioma and 2 human lung cell lines were used for sequence analysis of mRNA (cDNA) for isoform 1 and isoform 2 of the NF2 gene products and genomic DNA (gDNA) for the NF2 gene.

| Cell Line | cDNA (isoforms 1 & 2) | gDNA |
|---|---|---|
| A549 | Both isoforms, no changes | Full coverage, no change |
| NCI-H28 | Both isoforms, no changes | Full coverage, no change |
| *NCI-H226 | Neither amplified | Missing exon 1 |
| *NCI-2052 | Both, Arg341Stp | Full coverage, Arg341Stp |
| NCI-H2452 | Both isoforms, no changes | Full coverage, no change |
| MSTO-211H | Both isoforms, no changes | Full coverage, no change |
| *SW-1573 | Neither amplified | Missing exon 1-4 |

Example 9

Comparison of the Levels of FAK and pFAK in NF2 Mutant and NF2 Wild-Type Cells

Figure 2:
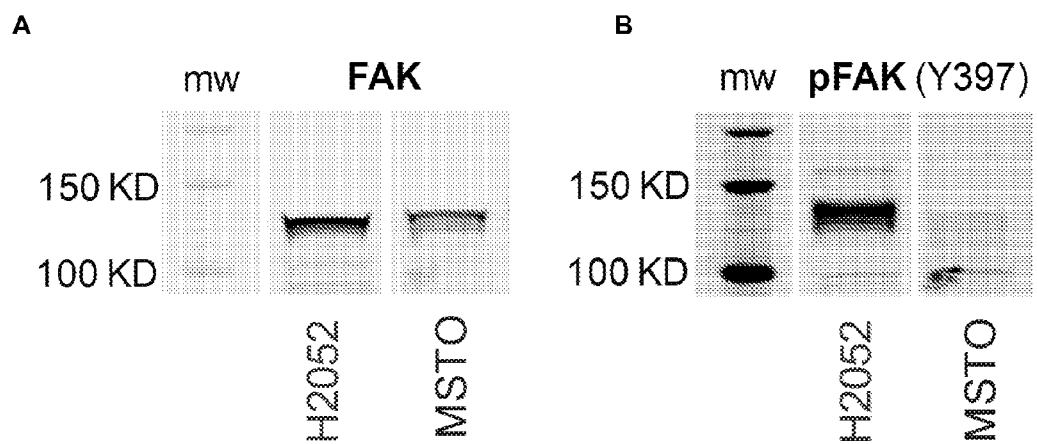
FIG. 2 shows images of western blot detection of the protein levels of FAK [FIG. 2A] and phosphorylated FAK (pFAK) [FIG. 2B] in the human cell line NCI-H2052 (NF2 mutant in which merlin isoform 1 is not detected) and the human cell line MSTO-211H (wild-type NF2 in which merlin isoform 1 is detected).

To investigate further the relationship between merlin isoform 1 expression, FAK expression, FAK phosphorylation status, and response to FAK inhibition, 2 cell lines were selected for evaluation. NCI-H2052 was selected as the NF2 mutant cell line, which lacks expression of merlin isoform 1 protein and MSTO-211H as the NF2 wild-type cell line, which exhibits expression of merlin isoform 1 protein. The level of FAK and pFAK (Y397) expression was characterized by western blots using whole cell lysates obtained from cells grown in the methylcellulose anchorage-independent conditions, as shown in FIG. 2. Western blots indicate a slightly higher level of total FAK protein in the NF2 mutant cell line compared to the NF2 wild-type line (FIG. 2A). More significantly, the level of pFAK was greatly elevated in the NCI-H2052 NF2 mutant cell line compared to the MSTO-211H NF2 wild-type cell line (FIG. 2B). The same amount of protein was loaded on the gel for the samples as determined by protein concentration. The amount of actin detected on the western blot with an anti-actin antibody (not shown) substantiated equal transfer to the blotting membrane. Thus, although a small increase in the level of total FAK protein was observed in the mesothelioma cell line with mutant NF2, the level of phosphorylated, and presumably activated FAK, was substantially increased in the NF2 mutant cell line.

Example 10

Evaluation of Cell Growth Inhibition by FAK Inhibitor Compound A

The growth inhibitory activity of the FAK inhibitor Compound A was evaluated in the 2 mesothelioma cell lines grown in the anchorage-independent methylcellulose assay (Table 2), and further re-tested in these 2 cell lines alongside an additional 4 cell lines (Table 3).

In the initial anchorage-independent assay, although both cell lines had a growth inhibitory response as quantified by gIC$_{50}$ values, there was a large difference between the sensitivities of the two cell lines (Table 2). The NF2 mutant (i.e., that does not express isoform 1 protein from the NF2 gene and is thus called merlin negative) NCI-H2052 mesothelioma cell line responded to approximately 19 fold less compound compared to the NF2 wild-type (which do express isoform 1 protein of NF2 and are called merlin positive) MSTO-211H cells to induce 50% inhibition of growth. In addition, the NF2 wild-type MSTO-211H cells displayed an increase in the cell population over the course of the 6 day assay even in the presence of the highest concentration (~30 µM) of Compound A. This was observed from the Ymin-T0 value of 343%, an increase from 100% at the start of the assay. In contrast, the NF2 mutant cell line, NCI-H2052, had the same number of cells at the end of the assay compared to the start, the Ymin-T0 value was essentially 0 (−3%). No change in the number of cells suggests Compound A was able to completely block cell growth and proliferation for the duration of the assay in the NF2 mutant cell line.

TABLE 2

| Cell Line | Growth Inhibition gIC$_{50}$ (nM) | Net Pop. change Ymin-T0 (%) |
| --- | --- | --- |
| MSTO-211H | 3588 | 343 |
| NCI-H2052 | 186 | −3 |

In the second anchorage-independent assay, the isoform 1 protein gene product of NF2 (i.e. merlin isoform 1 protein, or merlin protein for short) was determined by western blot. All 5 merlin negative cell lines had potent growth inhibition (gIC$_{50}$ values<250 nM) while the merlin positive cell line required ~10 µM of Compound A for 50% growth inhibition. The cell population did not increase during the assay in the merlin negative cell lines and some cell lines demonstrated net cell kill (negative Ymin-T0 values). [Note that a Ymin-T0 value of 0% indicates no change in the number of cells during the assay.] The merlin positive MSTO-211H cell line had a net increase in the cell population in the presence of Compound A as indicated by the positive Ymin-T0 value. These results are shown in Table 3.

TABLE 3

| merlin status | Cell Line | Growth Inhibition gIC$_{50}$ (nM) | Net Population Change Ymin-T0 (%) |
| --- | --- | --- | --- |
| negative | Mero-41 | 54 | −54 |
| negative | Mero-82 | 59 | −22 |
| negative | Mero-14 | 63 | −55 |
| negative | NCI-H226 | 196 | −18 |
| negative | NCI-H2052 | 236 | 7 |
| positive | MSTO-211H | 10859 | 367 |

Example 11

Clinical Study Design

A multi-part, Phase I study was designed to determine the maximum tolerated dose (MTD), safety, tolerability, pharmacokinetics (PK), pharmacodynamics (PD), and anti-tumor activity of Compound A in patients with advanced solid tumors. Part 1 of the study identified the MTD using a dose escalation procedure, and is described herein. Parts 2-3 are ongoing. Part 2 further explores the safety and tolerability of Compound A at or below the MTD, and Part 3 evaluates the pharmacodynamics of Compound A at doses at and below the MTD. Part 4 was not opened for patient accrual at the time of this summary and will explore the safety, tolerability, pharmacokinetics and clinical activity of Compound A in patients with recurrent glioblastoma multiforme. Part 5 was not opened for patient accrual at the time of this summary and will explore the pharmacokinetics of Compound A over several weeks of administration. Patients with mesothelioma were eligible to participate, e.g, in Part 1, of the study. Patients with mesothelioma were eligible to participate in Parts 1-3 of the study at the time the data below were collected.

Inclusion/Exclusion Criteria:

Patients 18 years old with advanced solid tumors with histologically or cytologically confirmed diagnosis of a solid tumor malignancy that was not responsive to accepted standard therapies or for which there is no standard or curative therapy were eligible. All patients provided signed informed consent. Patients were required to have the ability to swallow and retain oral medication, adhere to protocol-defined birth control measures for males and females of childbearing potential, exhibit adequate organ system function, and provide archival tumor specimens as defined in the protocol. In Parts 2-3 of the study, patients with tumors reported in the literature to overexpress FAK that are not responsive to accepted standard therapies or for which there were no standard or curative therapies were included. Subjects in Part 3 were also required to have solid tumors amenable to biopsy.

Patients were excluded that had an investigational anticancer drug within 28 days or 5 half-lives with a minimum duration of 10 days from prior therapy or chemotherapy within the last 3 weeks (6 weeks for prior mitomycin C or nitrosureas) or any major surgery, radiotherapy, or immunotherapy within the last 4 weeks. Patients with an active gastrointestinal disease known to interfere with the pharmacokinetics of drugs or prior resection of the small intestine were ineligible. Other exclusion criteria included unresolved toxicity>Grade 1 from previous anticancer therapy except alopecia, QTcF interval>450 msecs in males (470 in females) or congenital long QT syndrome, history of acute coronary syndromes, Class II-IV heart failure as defined by the New York Heart Association, symptomatic or untreated brain metastases, primary malignancy of the central nervous system (in Parts 1-3), nursing females, consumption of dietary substances or prohibited medications as defined in the protocol, or any serious and/or unstable pre-existing medical, psychiatric, or other condition that could interfere with subject safety or obtaining informed consent.

Assessment of Safety and Efficacy:

Measurements to evaluate safety included weight, heart rate, blood pressure, temperature, clinical laboratory tests, 12-lead ECG, and neurologic and physical evaluation. Adverse events were assessed throughout the study using the CTCAE v4.0, Common Terminology Criteria for Adverse Events (CTCAE) Version 4.0, US Department of Health and Human Services, National Institutes of Health, National Cancer Institute, May 2009.

Disease assessment was performed at screening and every 6 weeks after the start of dosing. Response was recorded as complete response (CR), partial response (PR), stable disease (SD), or progressive disease (PD) according to the RECIST Version 1.1.

Example 12

Immunohistochemical Determination of Merlin Status in Biopsies of Patients Enrolled in the Clinical Trial To determine if loss of merlin in the current Phase I mesothelioma population was predictive of response to Compound A, merlin levels were assessed in archival tissue (FFPE) collected at screening by immunohistochemistry (IHC), and the result correlated to clinical endpoint of median progression free survival (PFS).

A custom IHC assay was developed by Mosaic laboratories, Inc, employing a rabbit polyclonal antibody (Santa Cruz Biotechnology, Inc, catalog # SC332) using a dilution of 1:1600. The antibody signal was evaluated by Envision+rabbit HRP (DAKO) detection kit, and the staining intensity (Grade 0-3+) was used to categorize merlin status (merlin positive=wildtype or merlin negative=loss of merlin) of the clinical samples tested.

The threshold for the call, a fixed H-score (10 or >Grade 2+staining=Merlin positive and <10 in Grade 2+=Merlin negative) was derived using a mesothelioma cell line validation panel comprising six cell lines (SW1573, NCI-2052, NCI-H226, NCI-H28, NCI-2452 and MSTO-211H procured from ATCC) exhibiting differential merlin expression. Subcellular localization (i.e nucleus, cytoplasm and membrane) of the signal was documented but not used for determining the threshold. The call-threshold was further optimized during the technical validation of the assay through accuracy and precision studies addressing the inter-day and intra-day variability of the assay. The presence or absence of merlin in the same cell lines used for assay validation was independently confirmed by western blotting and Sanger sequencing of the cDNA and genomic DNA.

Loss of merlin in the cell lines tested was attributed to 3 observations: loss of exon 1 encoding the start codon for NCI-H226, loss of exons 1-4 for SW-1573 and presence of a stop codon (Arg 341) in exon 11 for NCI-2052. For clinical correlation, 24 of the 29 available mesothelioma samples were tested for merlin employing the custom GSK NF2-1 IHC assay and the merlin status correlated to median PFS (please see efficacy analysis). Results obtained indicate merlin as a potential predictive biomarker for clinical activity for Compound A in patients with recurrent mesothelioma.

Statistical Analysis:

Descriptive statistics were used for analysis of demographic, clinical laboratory, and disease characteristics. Progression free survival was determined using the Kaplan-Meier method, which is well known in the art and is described in Kaplan E L and Meier P, 1958), "Non-parametric estimation from Incomplete Observations JASA 53: 457-481, and Lee E T, Statistical Methods for Survival Data Analysis, 2nd edition, John Wiley and Sons, New York, 1992, each of which is incorporated by reference in the entirety.

Results:

Demographic characteristics for the all patient and mesothelioma patient populations are provided in Table 4.

TABLE 4

Demographic Characteristics

| Variable | All Patients No. (%) | Mesothelioma Patients No. (%) |
|---|---|---|
| No. of Patients | 62 (100) | 29 (100) |
| Median age (range) | 61 (21-84) | 64 (47-84) |
| Gender | | |
| Females | 23 (37) | 6 (21) |
| Males | 39 (63) | 23 (79) |
| Ethnicity | | |
| Hispanic/Latino | 3 (5) | 3 (10) |
| Non-Hispanic/Non-Latino | 59 (95) | 26 (90) |

Evaluation of Merlin Status:

Of 29 patients with mesothelioma, 14 were merlin negative, 9 were merlin positive, and six were unknown, as measured by IHC (as described in Example 12) of biopsy samples obtained from patients.

Figure 4:
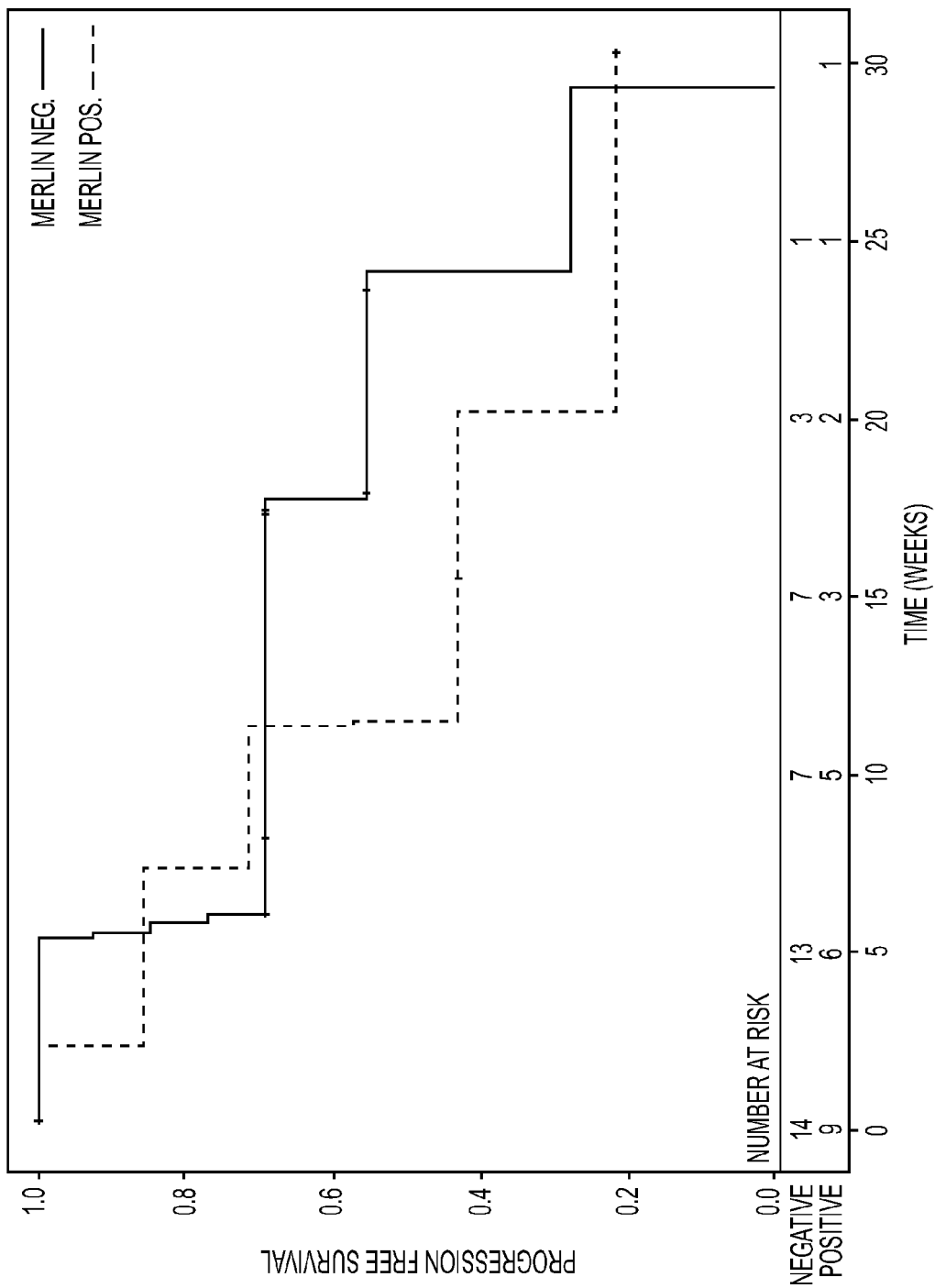
FIG. 4 is a graph showing Kaplan-Meier Progression Free Survival of patients treated with Compound A by merlin isoform 1 status.
Figure 5:
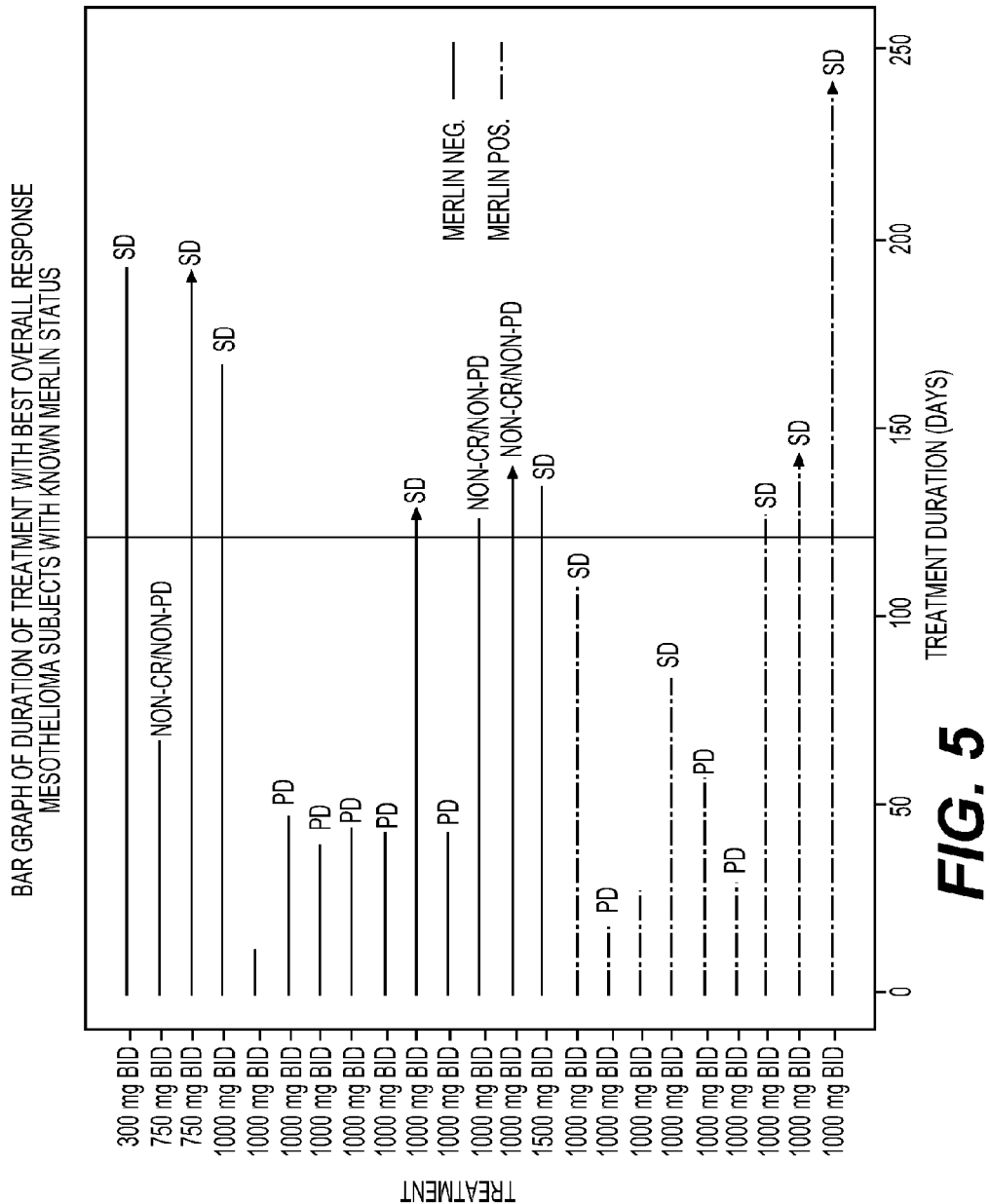
FIG. 5 is a bar graph of the duration of treatment in patients treated with Compound A, where merlin isoform 1 status is noted.
Figure 6:
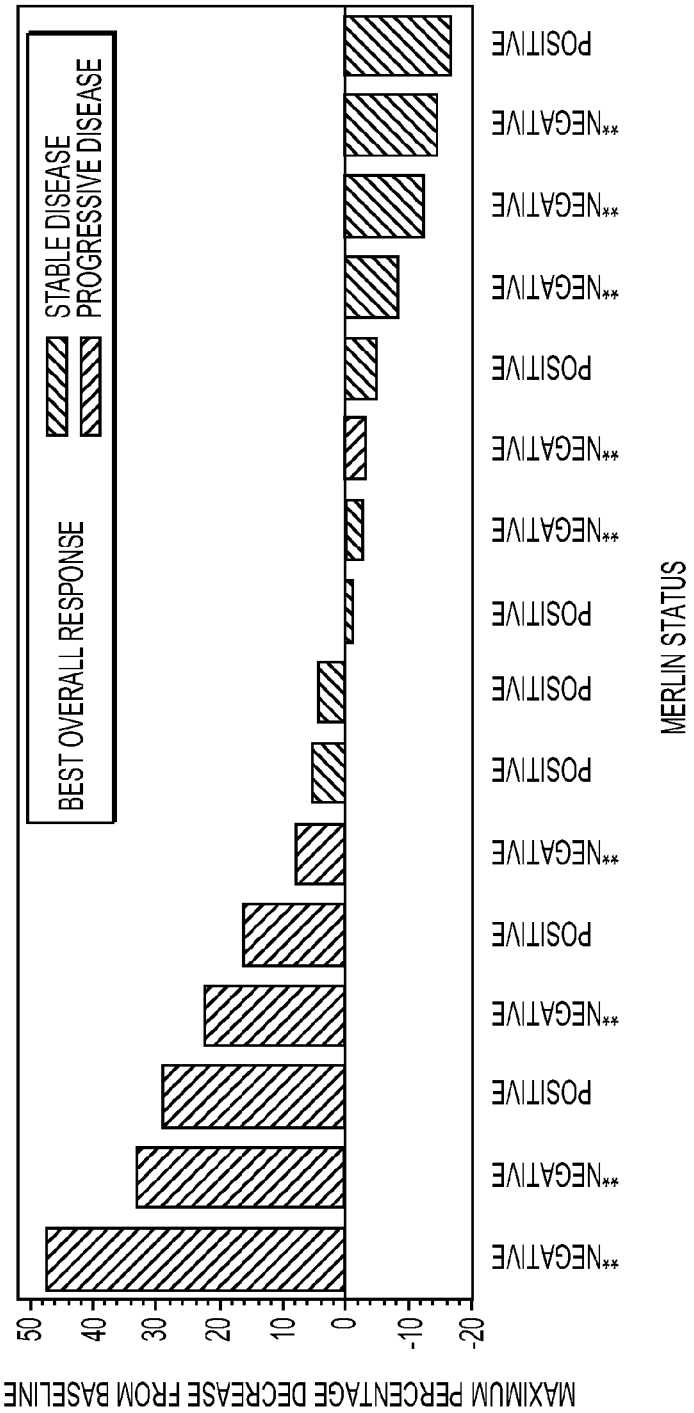
FIG. 6 is a bar graph of the percent change from baseline in tumor measurement (investigator assessed) at time of best response, as determined by RECIST criteria, in patients treated with Compound A, where merlin isoform 1 status is noted.

Efficacy Analysis:

In patients with mesothelioma, 26 had radiologic assessments after starting therapy. Three patients were removed from the study prior to radiologic assessments. As best response to treatment, fourteen patients had SD, three patient had non-CR/non-PD, and 9 patients had PD. Percent change from baseline in tumor burden at time of best response is shown in FIG. 6. Only patients with measurable disease at baseline and who had post-baseline scans were included on this graph. While no patients experienced a PR or CR, minor responses in some patients with mesothelioma were seen (e.g. tumor shrinkage, but not the level required for PR). The overall median progression free survival (PFS) was 17.7 weeks (95% CI 9.7, 24.1). The median PFS in merlin negative and positive subjects were 24.1 (n=14; 95% CI 6.0, 29.3) and 11.4 (n=9; 95% CI 7.3, undefined) respectively (FIG. 4). Treatment duration for each patient is shown in FIG. 5, comparing Merlin negative to Merlin positive patients. Seven of 14 Merlin negative patients remained on study for more than four months, compared with three of nine for Merlin positive patients. The dose received is shown in the left-hand column of the graph.

While the preferred embodiments of the invention are illustrated by the above, it is to be understood that the invention is not limited to the precise instructions herein disclosed and that the right to all modifications coming within the scope of the following claims is reserved.

REFERENCES

1. McLean, G. W., et al., *The role of focal-adhesion kinase in cancer—a new therapeutic opportunity.* Nat Rev Cancer, 2005. 5(7): p. 505-15.
2. Mitra, S. K., D. A. Hanson, and D. D. Schlaepfer, *Focal adhesion kinase: in command and control of cell motility.* Nat Rev Mol Cell Biol, 2005. 6(1): p. 56-68.
3. Zhao, J. and J. L. Guan, *Signal transduction by focal adhesion kinase in cancer.* Cancer Metastasis Rev, 2009.
4. Guan, J. L., J. E. Trevithick, and R. O. Hynes, *Fibronectin/integrin interaction induces tyrosine phosphorylation of a 120-kDa protein.* Cell Regul, 1991. 2(11): p. 951-64.
5. Kornberg, L. J., et al., *Signal transduction by integrins: increased protein tyrosine phosphorylation caused by clustering of beta 1 integrins.* Proc Natl Acad Sci USA, 1991. 88(19): p. 8392-6.
6. Kanner, S. B., et al., *Monoclonal antibodies to individual tyrosine-phosphorylated protein substrates of oncogene-encoded tyrosine kinases.* Proc Natl Acad Sci USA, 1990. 87(9): p. 3328-32.
7. Schaller, M. D., et al., *pp 125FAK a structurally distinctive protein-tyrosine kinase associated with focal adhesions.* Proc Natl Acad Sci USA, 1992. 89(11): p. 5192-6.
8. Schultze, A. and W. Fiedler, *Therapeutic potential and limitations of new FAK inhibitors in the treatment of cancer.* Expert Opin Investig Drugs, 2010. 19(6): p. 777-88.
9. Schwock, J., N. Dhani, and D. W. Hedley, *Targeting focal adhesion kinase signaling in tumor growth and metastasis.* Expert Opin Ther Targets, 2010. 14(1): p. 77-94.
10. Evans, D. G., *Neurofibromatosis type 2 (NF2): a clinical and molecular review.* Orphanet J Rare Dis, 2009. 4: p. 16.

11. Yi, C., et al., *A tight junction-associated Merlin-angiomotin complex mediates Merlin's regulation of mitogenic signaling and tumor suppressive functions.* Cancer Cell, 2011. 19(4): p. 527-40.
12. Houshmandi, S. S., et al., *The neurofibromatosis 2 protein, merlin, regulates glial cell growth in an ErbB2-and Src-dependent manner.* Mol Cell Biol, 2009. 29(6): p. 1472-86.
13. Stamenkovic, I. and Q. Yu, Merlin, *a "magic" linker between extracellular cues and intracellular signaling pathways that regulate cell motility, proliferation, and survival.* Curr Protein Pept Sci, 2010. 11(6): p. 471-84.
14. Schneider, M. D., *Development. A cardiac nonproliferation treaty.* Science, 2011. 332(6028): p. 426-7.
15. Robinson, B. W. and R. A. Lake, *Advances in malignant mesothelioma.* N Engl J Med, 2005. 353(15): p. 1591-603.
16. Poulikakos, P. I., et al., *Re-expression of the tumor suppressor NF2/merlin inhibits invasiveness in mesothelioma cells and negatively regulates FAK.* Oncogene, 2006. 25(44): p. 5960-8.

What is claimed is:

1. A method of treating cancer in a human in need thereof, comprising determining the presence or absence of a detectable amount of a gene product of the Neurofibromin-2 (NF2) gene in a sample from said human, and administering to said human an effective amount of a focal adhesion kinase (FAK) inhibitor, or a pharmaceutically acceptable salt thereof, if no gene product or no isoform 1 gene product is detected.

2. The method of claim 1, further comprising detecting phosphorylated FAK (p-FAK).

3. The method of claim 1, further comprising detecting loss of function of an isoform 1 gene product of NF2 if the isoform 1 gene product of the NF2 gene is present.

4. The method of claim 3, further comprising administering to said human an effective amount of a FAK inhibitor, or a pharmaceutically acceptable salt thereof, if a detectable amount of an isoform 1 gene product of the NF2 gene is present and loss of function of the isoform 1 gene product of NF2 gene is detected.

5. The method of any of claim 1, wherein the presence or absence of gene product or isoform 1 gene product of the NF2 gene is determined using immunohistochemistry (IHC).

6. The method of claim 5, wherein IHC comprises using an antibody that binds isoform 1 gene product of the NF2 gene but does not bind other isoform gene products of the NF2 gene.

7. The method of claim 1, wherein said treatment with a FAK inhibitor results in an increase in Progression Free Survival (PFS) time.

8. The method of claim 7, wherein the increase in PFS time is clinically meaningful.

9. The method of claim 7, wherein the increase in PFS time is statistically significant.

10. The method of claim 1, wherein the sample comprises one or more tumor cells.

11. The method of claim 1, wherein the gene product of the NF2 gene is a protein, or a functional fragment thereof.

12. A method of treating cancer in a human in need thereof comprising determining the presence or absence of a detectable amount of merlin or a functional fragment thereof from a tumor sample from said human, and administering to said human an effective amount of 2-[(5-chloro-2-{[3-methyl-1-(1-methylethyl)-1H-pyrazol-5-yl]amino}-4-pyridinyl) amino]-N-(methyloxy)benzamide, or a pharmaceutically acceptable salt thereof, if no merlin or functional fragment thereof is detected.

13. A method of treating merlin negative cancer in a human in need thereof comprising administering a therapeutically effective amount of a FAK inhibitor, or a pharmaceutically acceptable salt thereof, to said human.

14. The method of claim 1 or claim 13, wherein said FAK inhibitor is 2-[(5-chloro-2-{[3-methyl-1-(1-methylethyl)-1H-pyrazol-5-yl]amino}-4-pyridinyl)amino]-N-(methyloxy)benzamide, or a pharmaceutically acceptable salt thereof.

15. The method of claim 1 or claim 14, wherein the cancer is selected from the group consisting of schwannoma, meningioma, ependymoma, mesothelioma, glioblastoma, melanoma thyroid cancer, bladder cancer, skin cancer, stomach cancer, bone cancer, kidney cancer, breast cancer, and intestinal cancer.

16. The method of claim 15, wherein the cancer is mesothelioma.

* * * * *

UNITED STATES PATENT AND TRADEMARK OFFICE
CERTIFICATE OF CORRECTION

| | |
|---|---|
| PATENT NO. | : 9,192,604 B2 |
| APPLICATION NO. | : 14/128007 |
| DATED | : November 24, 2015 |
| INVENTOR(S) | : Kurt R. Auger et al. |

It is certified that error appears in the above-identified patent and that said Letters Patent is hereby corrected as shown below:

In the claims,

In column 51, lines 40 to 42, claim 5, should be corrected, removing the words 'any of' from line 40, to read as follows:

5. The method of claim 1, wherein the presence or absence of gene product or isoform 1 gene product of the NF2 gene is determined using immunohistochemistry (IHC).

Signed and Sealed this
Sixteenth Day of August, 2016

Michelle K. Lee
*Director of the United States Patent and Trademark Office*